United States Patent
Deasy et al.

(10) Patent No.: US 11,568,618 B2
(45) Date of Patent: Jan. 31, 2023

(54) SYSTEMS AND METHODS FOR DESIGNING AND MANUFACTURING CUSTOM IMMOBILIZATION MOLDS FOR USE IN MEDICAL PROCEDURES

(71) Applicant: MEMORIAL SLOAN KETTERING CANCER CENTER, New York, NY (US)

(72) Inventors: Joseph Owen Deasy, New York, NY (US); Paul R. Booth, New York, NY (US); Nancy Lee, New York, NY (US); Dale Michael Lovelock, New York, NY (US)

(73) Assignee: Memorial Sloan Kettering Cancer Center, New York, NY (US)

(*) Notice: Subject to any disclaimer, the term of this patent is extended or adjusted under 35 U.S.C. 154(b) by 546 days.

(21) Appl. No.: 16/634,465

(22) PCT Filed: Jul. 27, 2018

(86) PCT No.: PCT/US2018/044145
§ 371 (c)(1),
(2) Date: Jan. 27, 2020

(87) PCT Pub. No.: WO2019/023610
PCT Pub. Date: Jan. 31, 2019

(65) Prior Publication Data
US 2021/0090716 A1    Mar. 25, 2021

Related U.S. Application Data

(60) Provisional application No. 62/538,506, filed on Jul. 28, 2017.

(51) Int. Cl.
*G06T 19/20* (2011.01)
*G16H 30/20* (2018.01)
(Continued)

(52) U.S. Cl.
CPC ............ *G06T 19/20* (2013.01); *A61B 5/0064* (2013.01); *A61B 5/055* (2013.01); *A61B 5/1078* (2013.01);
(Continued)

(58) Field of Classification Search
None
See application file for complete search history.

(56) References Cited

U.S. PATENT DOCUMENTS

2011/0047706 A1* 3/2011 Hiebert ................. A61F 5/3776
5/621
2012/0289759 A1* 11/2012 Lynch .................. A61B 6/0442
128/870
(Continued)

FOREIGN PATENT DOCUMENTS

ES    2585265 A1    10/2016

OTHER PUBLICATIONS

Stephen Laycock, et al., "Towards the Production of Radiotherapy Treatment Shells on 3D printers using data derived from DICOM CT and MRI: preclinical feasibility studies", Aug. 22, 2014, Cambridge University Press, Journal of Radiotherapy in Practice (2015), vol. 14, Issue 1, pp. 92-98.*
(Continued)

Primary Examiner — Robert Bader
(74) Attorney, Agent, or Firm — Foley & Lardner LLP

(57) ABSTRACT

Described herein are systems and methods of processing immobilization molds for application of treatment, A computing system may generate a three-dimensional mold model of immobilization mold within with a subject is to be positioned for application of a treatment. The computing system may subtract a three-dimensional scan of at least a portion of the subject from the three-dimensional mold model to define an opening therein. The computing system
(Continued)

may remove, from the three-dimensional mold model, a first portion to define an imprint in the opening from a first axis along which the subject is to enter. The computing system may remove, from a second portion of the three-dimensional mold model remaining with the removal of the first portion, inward protrusions into the imprint of relative to the second axis intersecting the first axis.

20 Claims, 20 Drawing Sheets

(51) Int. Cl.
*A61B 5/00* (2006.01)
*A61B 5/055* (2006.01)
*A61B 5/107* (2006.01)
*A61B 6/03* (2006.01)
*A61B 6/04* (2006.01)
*A61B 8/00* (2006.01)
*A61N 5/10* (2006.01)

(52) U.S. Cl.
CPC .............. *A61B 5/70* (2013.01); *A61B 6/032* (2013.01); *A61B 6/0421* (2013.01); *A61B 8/40* (2013.01); *A61N 5/10* (2013.01); *G16H 30/20* (2018.01); *A61N 2005/1097* (2013.01); *G06T 2219/2021* (2013.01)

(56) References Cited

U.S. PATENT DOCUMENTS

| | | |
|---|---|---|
| 2014/0315153 A1 | 10/2014 | Kitching et al. |
| 2014/0330417 A1 | 11/2014 | Keane |
| 2015/0094838 A1 | 4/2015 | MacLaverty |
| 2015/0157822 A1 | 6/2015 | Karpas et al. |
| 2015/0269289 A1 | 9/2015 | Kim et al. |
| 2016/0339607 A1 | 11/2016 | Munoz et al. |
| 2017/0020623 A1 | 1/2017 | Glossop |
| 2018/0001547 A1* | 1/2018 | Cuypers ................ B33Y 80/00 |

OTHER PUBLICATIONS

Fisher, M., Applegate, C., Ryalat, M., Laycock, S., Hulse, M., Emmens, D., Bell, D., "Evaluation of 3-D Printed Immobilisation Shells for Head and Neck IMRT", Dec. 2014, Open Journal of Radiology, 2014, Scientific Research Publishing, Issue 4, pp. 322-328.*

International Search Report and Written Opinion, PCT/US2018/044145, Memorial Sloan Kettering Cancer Center (dated Oct. 10, 2018).

\* cited by examiner

SYSTEMS AND METHODS FOR DESIGNING AND MANUFACTURING CUSTOM IMMOBILIZATION MOLDS FOR USE IN MEDICAL PROCEDURES

CROSS-REFERENCES TO RELATED APPLICATIONS

This application is a national stage application under 35 U.S.C. § 371 of International Patent Application No. PCT/US2018/0441457, titled "SYSTEMS AND METHODS FOR DESIGNING AND MANUFACTURING CUSTOM IMMOBILIZATION MOLDS FOR USE IN MEDICAL PROCEDURES," filed May 27, 2018, which claims priority under PCT Article 8 and PCT Rule 4.10 to U.S. Patent Provisional Application 62/538,506, titled "SYSTEMS AND METHODS FOR DESIGNING AND MANUFACTURING CUSTOM IMMOBILIZATION MOLDS FOR USE IN MEDICAL PROCEDURES," filed Jul. 28, 2017, each of which is incorporated herein by reference in its entirety.

TECHNICAL FIELD

The present application relates generally to the design and manufacture of custom immobilization molds specific to the subject for use in medical procedures.

BACKGROUND

To maximize the efficacy of a treatment (e.g., radiation therapy, etc.), the treatment may be applied to a specific location of a subject over a prescribed period of time. Translation, rotation, or any other movement by the subject during the application of the treatment may reduce the efficacy of the treatment. Present attempts to restrict such movement during treatment may include the use of enveloping receptacle to enclose the subject therein. The enveloping receptacle, however, may incorrectly position the subject with respect to the specific location at which the therapy is being applied. In addition, such techniques may lead to significant discomfort on the part of the subject, and in some cases, may induce adverse effects, such as claustrophobia. As such, these techniques may lead to suboptimal efficacy in the application of the treatment.

SUMMARY

Various embodiments disclosed herein provide apparatuses, systems, and methods related to the design and manufacture of custom immobilization molds specific to the subject for use in medical procedures, such as during the application of radiation therapy or during medical imaging and/or scanning procedures.

The present disclosure is directed to systems and methods for making custom immobilization molds. To make a custom immobilization mold that is specific to a given subject, a computing system may first acquire a scanned image of the subject from an imaging device. The scanned image may be acquired using at least one of an optical three-dimensional (3D) scan, a magnetic resonance imaging, a computed tomography scan, or a mechanical measurement using a pin table, among others. The scanned image may be of the subject lying prone or face down. The computing system may then convert or import the scanned image to a three-dimensional model (e.g., computer-aided design (CAD) model). In some embodiments, to convert the scanned image to the three-dimensional model, the computing system may perform contour segmentation techniques on the scanned image.

With the three-dimensional model generated, the computing system may then perform various image processing techniques on the three-dimensional model. In some embodiments, the computing system may apply a smoothing filter on the three-dimensional model to reduce noise and other features therefrom. In some embodiments, the computing system may then determine a negative of the three-dimensional model by subtraction (e.g., Boolean subtraction) to generate a mold block model. The computing system may perform additional image processing techniques on the mold block model (e.g., additional smoothing). Using the generated mold block model, the computing system may perform optimization techniques to allow the subject to fit into the immobilization mold. For each two-dimensional slice of the mold block model, the computing system may partition the slice into a left portion and a right portion. In each portion, the computing system may identify a global minimum and one or more local minima. The computing system may truncate the portion at the global minimum toward the side for inserting the subject into the mold. The computing system may identify one or more undercuts between pairs of local minima. The computing system may then remove the identified one or more undercuts from the remaining portion of the slice, thereby allowing easier manufacturing and permitting the subject to fit into the mold once it is formed.

In addition, the computing system may identify one or more locations in the mold block model to insert one or more accessories. Accessories may include restraining tensioners, retention blocks, and probes (e.g., ultrasound probes), among others. The one or more locations may be precisely determined by the computing system to allow the one or more accessories to fit against the subject once in the immobilization mold. In addition to identifying the locations, the orientation and alignment of any openings, slots, or regions within which such accessories are inserted may also be determined. In some embodiments, the precise position and alignment of the probe may allow the probe to be in contact with a surface (for example, skin) of the subject. In some embodiments, the computing system may remove portions of the model to accommodate the accessories.

Having generated the mold block model, the computing system may transfer the mold block model to a mold generator. The mold generator in turn may process and manufacture the physical immobilization mold using the mold block model. The mold generator may be a subtractive manufacturing device (e.g., a milling machine) or an additive manufacturing device (e.g., a three-dimensional printer) among others. In some embodiments, if the mold generator is a subtractive manufacturing device such as a milling machine, the mold generator may take a block mold and remove portions of the block mold corresponding to an imprint or a cavity to place the subject. In some embodiments, if the mold generator is an additive manufacturing device such as a three-dimensional printer, the mold generator may deposit material in the shape for the imprint or cavity to place the subject. The material used to manufacture the mold may have specific physical properties, such as ductility, plasticity, viscosity, elasticity, strain, strength, toughness, and viscoelasticity, among others. The material used to manufacture the mold may be radiolucent, radiotransparent, or radiopaque, among others depending on the type of medical procedure the mold is being used for. With the immobilization mold generated, a subject may be positioned within the mold for application of a therapy.

At least one aspect of the present disclosure is directed to a system for processing immobilization molds for application of treatment. The system may include a mold model generator executable on a computing system having one or more processor and memory. The mold model generator may generate a three-dimensional mold model of immobilization mold within with a subject is to be positioned for application of a treatment. The three-dimensional mold model may be generated by subtracting, from a first composite space of the three-dimensional mold model, a second composite space corresponding to a three-dimensional scan of at least a portion of the subject to define an opening within the three-dimensional mold model. The three-dimensional mold model may be generated by removing, from the three-dimensional mold model, to define an imprint in the opening, a first portion along a first axis in which the subject is to enter the immobilization mold. The three-dimensional mold model may be generated by identifying, from a second portion of the three-dimensional mold model remaining after the removal of the first portion, one or more inward protrusions into the imprint of the three-dimensional mold model relative to a second axis intersecting the first axis. The three-dimensional mold model may be generated by removing, from the three-dimensional mold model, the identified one or more inward protrusions relative to the second axis.

In some embodiments, the system may include an accessory positioner executable on the computing system. In some embodiments, the accessory positioner may identify, within the three-dimensional mold model, a position at which to insert an accessory into the immobilization mold. The accessory may include at least one of a tensioner, an anchoring mechanism, a sensor, a probe, or a treatment application device. In some embodiments, the accessory positioner may determine a third portion about the position within the three-dimensional mold model corresponding to dimensions of the accessory to be inserted. In some embodiments, the accessory positioner may remove the third portion of at least a part of the second portion of the three-dimensional mold model for insertion of the accessory. In some embodiments, the accessory positioner may add the third portion to the three-dimensional mold model for insertion of the accessory.

In some embodiments, the mold model generator may generate the three-dimensional mold model by identifying a plurality of two-dimensional slices of the three-dimensional mold model after subtracting of the second composite space. In some embodiments, the mold model generator may, for each two-dimensional slice of the three-dimensional mold model after subtracting of the second composite space, generate the three-dimensional mold model by: identifying a first section and a second section of to divide the opening about the first axis; determining a first global extremum from the first section and a second global extremum from the second section within the opening relative to the second axis; and removing, from the three-dimensional mold, the first portion in the first section from the first global extremum relative to the first axis and the first portion in the second section from the second global extremum relative to the first axis.

In some embodiments, the mold model generator may generate the three-dimensional mold model by identifying a plurality of two-dimensional slices of the three-dimensional mold model after subtracting of the second composite space. In some embodiments, the mold model generator may, for each two-dimensional slice of the three-dimensional mold model after subtracting of the second composite space, generate the three-dimensional mold model by: identifying a first section and a second section to divide the opening about the first axis; determining a first plurality of extrema in the first section within the opening and a second plurality of extrema in the second section within the opening relative to the second axis; identifying, in the first section, a first inward protrusion of the one or more inward protrusions in the three-dimensional mold model at the two-dimensional slice based on the first plurality of extrema; identifying, in the second section, a second inward protrusion of the one or more inward protrusions in the three-dimensional mold model at the two-dimensional slice based on the second plurality of extrema; and removing the first inward protrusion and the second inward protrusion from the two-dimensional slice of the three-dimensional mold model.

In some embodiments, the mold model generator may generate the three-dimensional mold model by identifying a plurality of two-dimensional slices of the three-dimensional mold model after subtracting of the second composite space. In some embodiments, the mold model generator may generate the three-dimensional mold model by identifying, for each two-dimensional slice of the three-dimensional mold model after subtracting of the second composite space, one or more contiguous portions of the opening defined by subtracting the second composite space corresponding to the three-dimensional scan of the subject. In some embodiments, the mold model generator may generate the three-dimensional mold model by identifying, for each contiguous portion, a first section and a second section to divide the contiguous portion to remove the first portion and one or more inward protrusions.

In some embodiments, the system may include a mold model optimizer executable on the computing system. In some embodiments, the mold model optimizer may identify a manufacturing modality of a mold generator to manufacture the immobilization mold in accordance with the three-dimensional model. The manufacturing modality may include at least one of a subtractive manufacturing and an additive manufacturing. In some embodiments, the mold model optimizer may modify the three-dimensional mold model based on the identified manufacturing modality of the mold generator.

In some embodiments, the system may include a mold model optimizer executable on the computing system. The mold model optimizer may apply an image processing technique to the three-dimensional mold model after subtraction of the second composite space and the removal the first portion and the one or more inward protrusions. The image processing technique may include at least one of an autofix function, a smoothing filter, a mesh reduction function, and a depth contrast adjustment. In some embodiments, the system may include an imager interface executable on the computing system. The imager interface may acquire, from an imaging device, a three-dimensional scan of the subject. In some embodiments, the system may include an image converter executable on the computing system. The image converter may convert the three-dimensional scan of the subject to the second composite space to subtract from the first composite space of the three-dimensional mold model.

At least another aspect of the present disclosure is directed to a method of processing immobilization molds for application of treatment. A computing system having one or more processors may generate a three-dimensional mold model of immobilization mold within with a subject is to be positioned for application of a treatment. The three-dimensional mold model may be generated by subtracting, from a first composite space of the three-dimensional mold model, a second composite space corresponding to a three-dimensional scan of at least a portion of the subject to define an opening within the three-dimensional mold model. The three-dimensional mold model may be generated by removing, from the three-dimensional mold model, to define an imprint in the opening, a first portion along a first axis in which the subject is to enter the immobilization mold. The three-dimensional mold model may be generated by identifying, from a second portion of the three-dimensional mold model remaining after the removal of the first portion, one or more inward protrusions into the imprint of the three-dimensional mold model relative to a second axis intersecting the first axis. The three-dimensional mold model may be generated by removing, from the three-dimensional mold model, the identified one or more inward protrusions relative to the second axis.

In some embodiments, the computing system may identify, within the three-dimensional mold model, a position at which to insert an accessory into the immobilization mold. The accessory may include at least one of a tensioner, an anchoring mechanism, a sensor, a probe, or a treatment application device. In some embodiments, the computing system may determine a third portion about the position within the three-dimensional mold model corresponding to dimensions of the accessory to be inserted. In some embodiments, the computing system may remove the third portion of at least a part of the second portion of the three-dimensional mold model for insertion of the accessory. In some embodiments, the computing system may add the third portion to the three-dimensional mold model for insertion of the accessory.

In some embodiments, the computing system may generate the three-dimensional mold model by identifying a plurality of two-dimensional slices of the three-dimensional mold model after subtracting of the second composite space. In some embodiments, the computing system may, for each two-dimensional slice of the three-dimensional mold model after subtracting of the second composite space, generate the three-dimensional mold model by: identifying a first section and a second section of to divide the opening about the first axis; determining a first global extremum from the first section and a second global extremum from the second section within the opening relative to the second axis; and removing, from the three-dimensional mold, the first portion in the first section from the first global extremum relative to the first axis and the first portion in the second section from the second global extremum relative to the first axis.

In some embodiments, the computing system may generate the three-dimensional mold model by identifying a plurality of two-dimensional slices of the three-dimensional mold model after subtracting of the second composite space. In some embodiments, the computing system may, for each two-dimensional slice of the three-dimensional mold model after subtracting of the second composite space, generate the three-dimensional mold model by: identifying a first section and a second section to divide the opening about the first axis; determining a first plurality of extrema in the first section within the opening and a second plurality of extrema in the second section within the opening relative to the second axis; identifying, in the first section, a first inward protrusion of the one or more inward protrusions in the three-dimensional mold model at the two-dimensional slice based on the first plurality of extrema; identifying, in the second section, a second inward protrusion of the one or more inward protrusions in the three-dimensional mold model at the two-dimensional slice based on the second plurality of extrema; and removing the first inward protrusion and the second inward protrusion from the two-dimensional slice of the three-dimensional mold model.

In some embodiments, the computing system may generate the three-dimensional mold model by identifying a plurality of two-dimensional slices of the three-dimensional mold model after subtracting of the second composite space. In some embodiments, the computing system may generate the three-dimensional mold model by identifying, for each two-dimensional slice of the three-dimensional mold model after subtracting of the second composite space, one or more contiguous portions of the opening defined by subtracting the second composite space corresponding to the three-dimensional scan of the subject. In some embodiments, the computing system may generate the three-dimensional mold model by identifying, for each contiguous portion, a first section and a second section to divide the contiguous portion to remove the first portion and one or more inward protrusions.

In some embodiments, the computing system may identify a manufacturing modality of a mold generator to manufacture the immobilization mold in accordance with the three-dimensional model. The manufacturing modality may include at least one of a subtractive manufacturing and an additive manufacturing. In some embodiments, the computing system may modify the three-dimensional mold model based on the identified manufacturing modality of the mold generator.

In some embodiments, the computing system may apply an image processing technique to the three-dimensional mold model after subtraction of the second composite space and the removal the first portion and the one or more inward protrusions. The image processing technique may include at least one of an autofix function, a smoothing filter, a mesh reduction function, and a depth contrast adjustment. In some embodiments, the computing system may acquire, from an imaging device, a three-dimensional scan of the subject. In some embodiments, the computing system may convert the three-dimensional scan of the subject to the second composite space to subtract from the first composite space of the three-dimensional mold model.

At least one other aspect of the present disclosure is directed to an apparatus for application of treatment. The apparatus may include an immobilization mold. The immobilization may have a first side and a second side. The immobilization mold may define an imprint. The imprint may contain a subject for application of the treatment along the first side through which the subject is to enter the immobilization mold. The imprint may lack any inward protrusions obstructing the entrance of the subject. The immobilization mold may define an opening through at least one of the first side and the second side into the imprint. The opening may hold a probe to be in contact with the subject contained in the imprint via a contact point of the opening. The probe may acquire data or apply a treatment to a localized area on the subject about the contact point.

In some embodiments, the probe may include a first block having a sensory aperture, a second block joined to the first block via one or more biasing elements and extrusion legs. The sensory aperture may be in contact with the subject at the contact point to acquire data or apply the treatment to the localized area. In some embodiments, the immobilization mold may be manufactured in accordance with a three-dimensional mold model provided from a computing system. The three-dimensional mold model may be generated by subtracting, from a first composite space of the three-dimensional mold model, a second composite space corresponding to a three-dimensional scan of at least a portion of the subject from the first composite space to define an opening within the three-dimensional mold model. The three-dimensional mold model may be generated by removing, from the three-dimensional mold model, a first portion to define the imprint in the opening from a first axis along which the subject is to enter the immobilization mold. The three-dimensional mold model may be generated by removing, from the three-dimensional mold model, the identified one or more inward protrusions into the imprint relative to the second axis orthogonal first axis.

In some embodiments, the immobilization mold may include a capping element inserted into the opening to secure the probe within the opening. In some embodiments, the immobilization mold may include one or more tensioners to restrain movement the subject contained within the imprint. In some embodiments, the immobilization mold may include one or more retention blocks along a third side opposite of the first side to prevent movement of the immobilization mold.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF THE DRAWINGS

It should be understood that the drawings primarily are for illustrative purposes and are not intended to limit the scope of the subject matter described herein. The drawings are not necessarily to scale; in some instances, various aspects of the subject matter disclosed herein may be shown exaggerated or enlarged in the drawings to facilitate an understanding of different features. In the drawings, like reference characters generally refer to like features (e.g., functionally similar and/or structurally similar elements).

FIGS. 5A-5D are screenshots showing applications of additional image processing techniques on a mold block model in processing immobilization molds, according to illustrative embodiments;

Figure 1A:
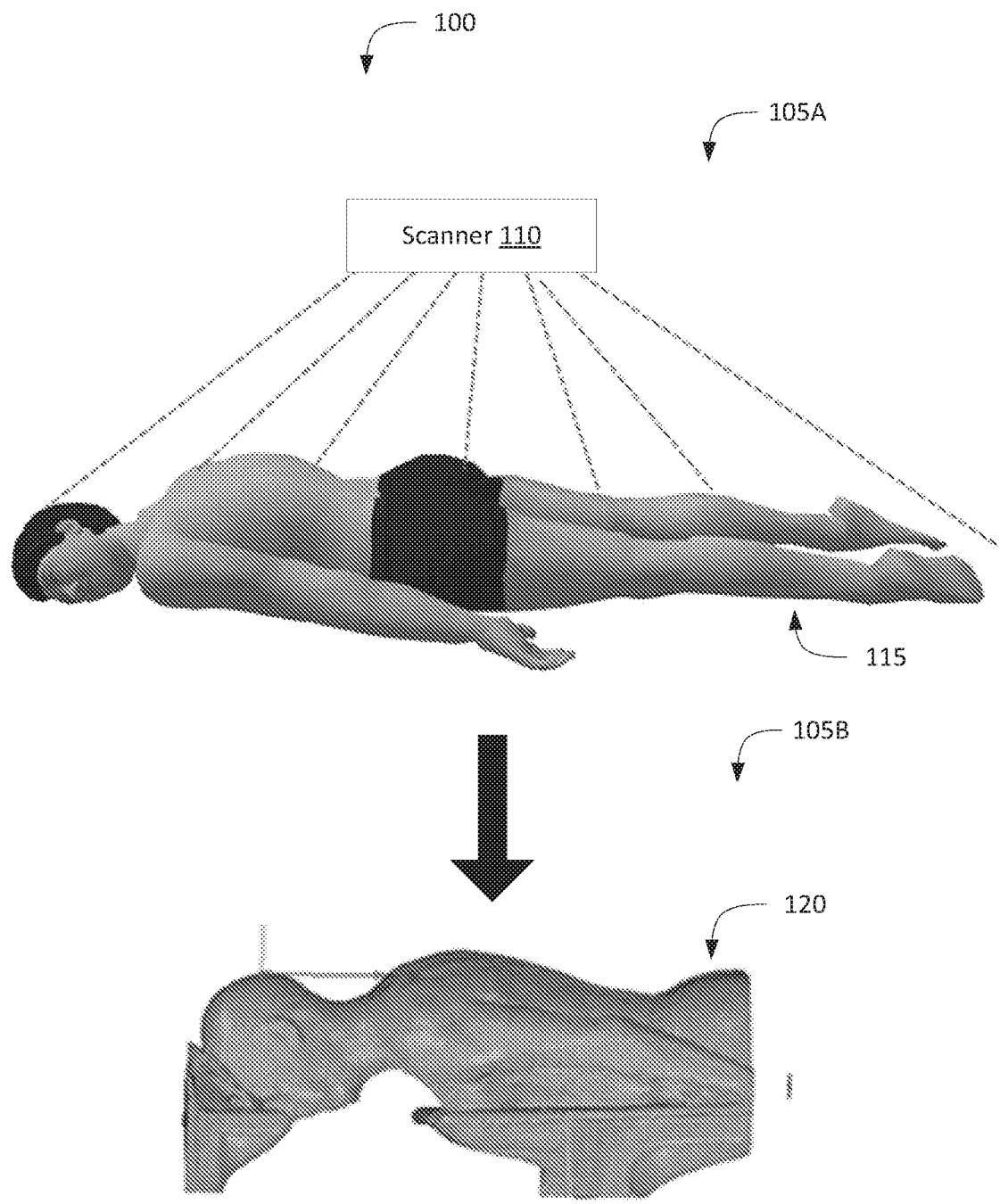
FIGS. 1A and 1B are sequence diagrams depicting a summary workflow of processing immobilization molds, according to an illustrative embodiment.

The features and advantages of the concepts disclosed herein will become more apparent from the detailed description set forth below when taken in conjunction with the drawings.

DETAILED DESCRIPTION

Following below are more detailed descriptions of various concepts related to, and embodiments of, inventive systems and methods for processing immobilization molds. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

Section A describes embodiments of designing and processing custom immobilization molds.

Section B describes a network environment and computing environment which may be useful for practicing various computing related embodiments described herein.

It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

A. Systems and Methods for Designing and Processing Custom Immobilization Molds

The present disclosure is directed to systems and methods for making custom immobilization molds. To make a custom immobilization mold that is specific to a given subject, a computing system may first acquire a scanned image of the subject from an imaging device. The scanned image may be acquired using at least one of an optical three-dimensional (3D) scan, a magnetic resonance imaging, a computed tomography scan, or a mechanical measurement using a pin table, among others. The scanned image may be of the subject lying prone or face down. The computing system may then convert or import the scanned image to a three-dimensional model (e.g., computer-aided design (CAD) model). In some embodiments, to convert the scanned image to the three-dimensional model, the computing system may perform contour segmentation techniques on the scanned image.

With the three-dimensional model generated, the computing system may then perform various image processing techniques on the three-dimensional model. In some embodiments, the computing system may apply a smoothing filter on the three-dimensional model to reduce noise and other features therefrom. In some embodiments, the computing system may then determine a negative of the three-dimensional model by subtraction (e.g., Boolean subtraction) to generate a mold block model. The computing system may perform additional image processing techniques on the mold block model (e.g., additional smoothing). Using the generated mold block model, the computing system may perform optimization techniques to allow the subject to fit into the immobilization mold. For each two-dimensional slice of the mold block model, the computing system may partition the slice into a left portion and a right portion. In each portion, the computing system may identify a global minimum and one or more local minima. The computing system may truncate the portion at the global minimum toward the side for inserting the subject into the mold. The computing system may identify one or more undercuts between pairs of local minima. The computing system may then remove the identified one or more undercuts from the remaining portion of the slice, thereby allowing easier manufacturing and permitting the subject to fit into the mold once it is formed.

In addition, the computing system may identify one or more locations in the mold block model to insert one or more accessories. Accessories may include restraining tensioners, retention blocks, and probes (e.g., ultrasound probes), among others. The one or more locations may be precisely determined by the computing system to allow the one or more accessories to fit against the subject once in the immobilization mold. In addition to identifying the locations, the orientation and alignment of any openings, slots, or regions within which such accessories are inserted may also be determined. In some embodiments, the precise position and alignment of the probe may allow the probe to be in contact with a surface (for example, skin) of the subject. In some embodiments, the computing system may remove portions of the model to accommodate the accessories.

Having generated the mold block model, the computing system may transfer the mold block model to a mold generator. The mold generator in turn may process and manufacture the physical immobilization mold using the mold block model. The mold generator may be a subtractive manufacturing device (e.g., a milling machine) or an additive manufacturing device (e.g., a three-dimensional printer) among others. In some embodiments, if the mold generator is a subtractive manufacturing device such as a milling machine, the mold generator may take a block mold and remove portions of the block mold corresponding to an imprint or a cavity to place the subject. In some embodiments, if the mold generator is an additive manufacturing device such as a three-dimensional printer, the mold generator may deposit material in the shape for the imprint or cavity to place the subject. The material used to manufacture the mold may have specific physical properties, such as ductility, plasticity, viscosity, elasticity, strain, strength, toughness, and viscoelasticity, among others. The material used to manufacture the mold may be radiolucent, radiotransparent, or radiopaque, among others depending on the type of medical procedure the mold is being used for. With the immobilization mold generated, a subject may be positioned within the mold for application of a therapy.

Figure 1B:
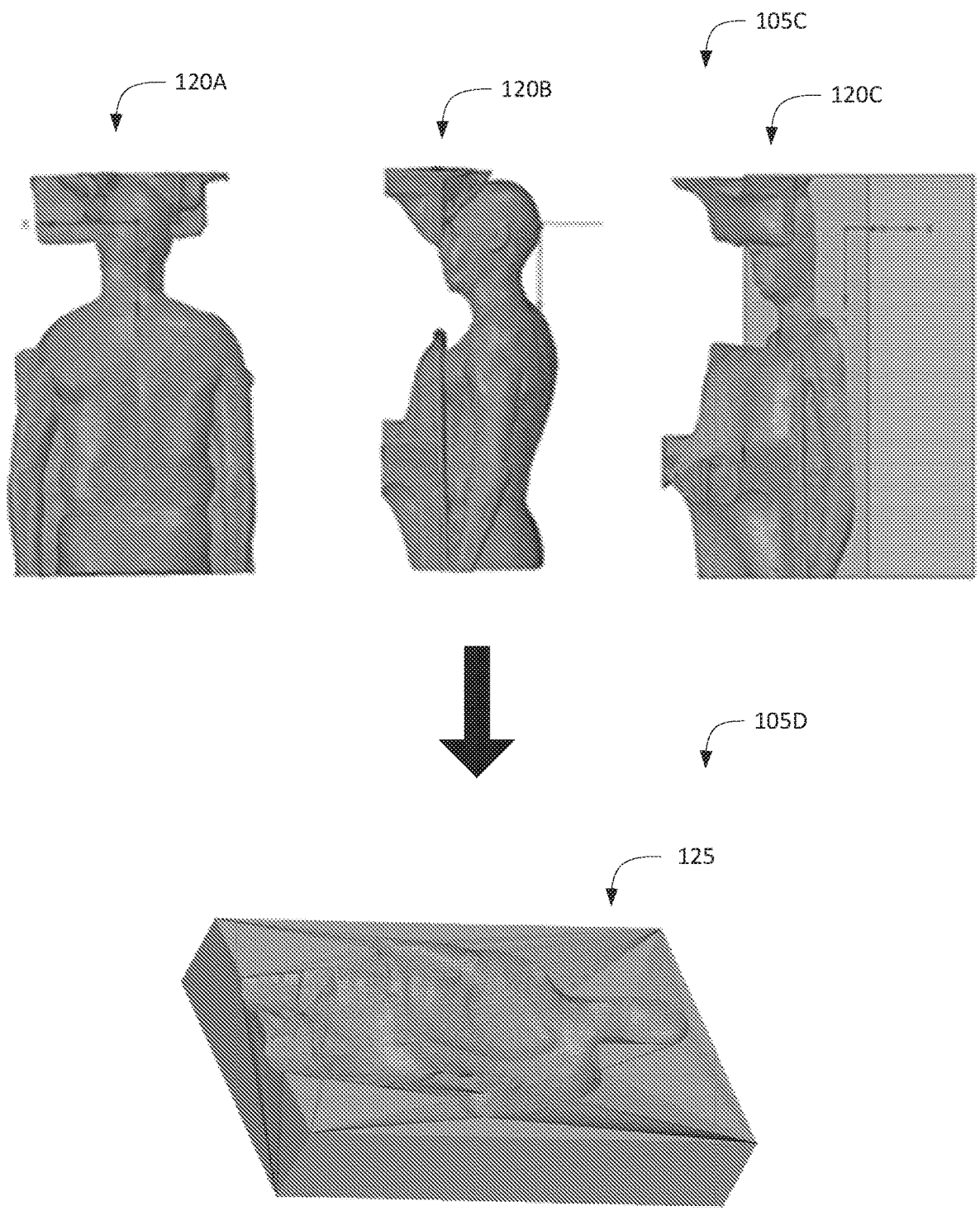

Referring first to FIGS. 1A and 1B, depicted is a summary sequence 100 for processing immobilization molds. At stage 105A, a scanner 110 may image a subject 115. The scanner may acquire an image of the subject 115 using three-dimensional optical scanning, a magnetic resonance imaging, a computed tomography scan, or a mechanical/tactile measurement using a pin table, among others. The scanned image of the subject 115 may be sent to a computing device for additional processing. At stage 105B, the computing device may generate a three-dimensional model 120 (e.g., a computer-aided design (CAD) model) of the scanned image received from the scanner 110. At stage 105C, using the generated three-dimensional model 120, the computing device may perform various image processing techniques. As shown, the computing device may reorient the three-dimensional model (models 120A and 120B). The computing device may also juxtapose the three-dimensional model of the subject to a generic mold block model (model 120C). At stage 105D, based on the juxtaposition, the computing device may generate a negative 125 of the three-dimension block onto the mold block model. The computing device may also perform additional image processing techniques on the mold block model.

Figure 2:
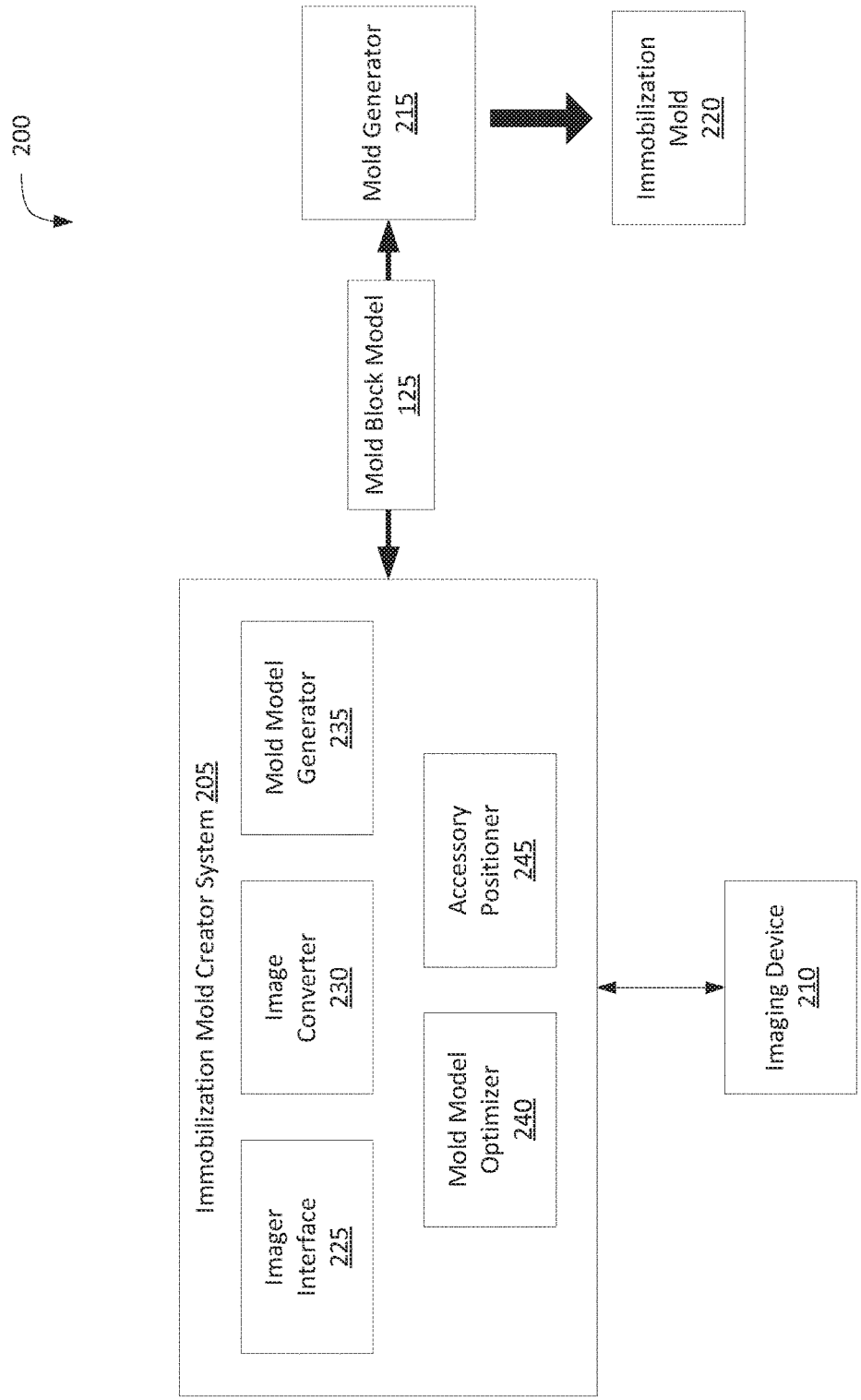
FIG. 2 is a block diagram depicting a system for processing immobilization molds, according to an illustrative embodiment.

Referring now to FIG. 2, depicted is a system 200 for processing immobilization molds. In brief overview, the system 200 may include an immobilization mold creator system 205, an imaging device 210, and a mold generator 215 to manufacture an immobilization mold 220. The immobilization mold creator system 205 may include an imager interface 225, an image converter 230, a mold model generator 235, a mold model optimizer 240, and an accessory positioner 245, among others, to transfer over the mold block model 125 to the mold generator 215.

Each of the above-mentioned elements or entities is implemented in hardware, or a combination of hardware and software, in one or more embodiments. For instance, each of these elements or entities could include any application, program, library, script, task, service, process or any type and form of executable instructions executing on hardware of the system, in one or more embodiments. The hardware includes circuitry such as one or more processors, for example, as described above in connection with FIGS. 9A-9D, in some embodiments, as detailed in section B.

The imager interface 225 may acquire an image of the subject 115 from the imaging device 210 (e.g., scanner 110). The imaging device 210 may be connected to the imager interface 225 via a wireless network or wired coupling. The imaging device 210 may be any type of scanner to acquire one or more two-dimensional images or a three-dimensional image (e.g., multiple slices of two-dimensional images) of the subject 115. In some embodiments, the imaging device 210 may be an optical scanner, sometimes referred to as a three-dimension scanner, such as a hand-held laser scanner, a structure-light scanner, a modulated light scanner, a time-of-flight laser, and a triangulation-based scanner, among others, that can generate a three-dimensional image of the subject 115. In some embodiments, the imaging device 210 may be a camera, such as a digital single-lens reflex (DSLR) camera, digital single lens translucent (DSLT), or an image sensor (e.g., charge-coupled device, active pixel sensor, etc.), among others, that can generate one or more two-dimensional images of the subject 115. In some embodiments, the imaging device 210 may be a magnetic resonance imaging (MRI) scanner that can generate a three-dimensional image of the subject 115. In some embodiments, the imaging device 210 may be a computed tomography (CT) scanner that can generate a three-dimensional image of the subject 115. In some embodiments, the imaging device 210 may be a mechanical/tactile sensor that can generate a three-dimensional image of the subject 115 from pressure or weight sensed at the device 210. Upon request, the imager interface 225 may send a request to the imaging device 210 to acquire the image of the subject 115. In turn, the imaging device 210 may capture the image of the subject 115 (e.g., two or three-dimensional), and may in turn return the captured image of the subject 115 to the imager interface 225. The imager interface 225 may subsequently receive the image of the subject 115 from the imaging device 210.

Using the image of the subject 115 captured by the imaging device 210, the image converter 230 may convert the image to a three-dimensional model 120. The three-dimensional subject model 120 may include composite space corresponding to the body of the subject 115 and negative space corresponding to the empty space around the body of the subject 115. The image converter 230 may use biomedical and anatomical engineering software, such as the MIMICS INNOVATION SUITE, to perform the conversion. If the image captured by the imaging device 210 is two-dimensional, the image converter 230 may apply various reconstruction algorithms to generate a three-dimensional image of the subject 115. Reconstruction algorithms may use depth cue pattern recognition (e.g., binocular disparity, focus, silhouette, shading, patterned, statistical patterns, etc.) in the one or more two-dimensional images to generate the three-dimensional image. The three-dimensional image constructed from the one or more two-dimensional images may include multiple slices of two-dimensional image.

Once the three-dimensional image of the subject 115 is acquired or constructed, the image converter 230 may generate the three-dimensional subject model 120 using various three-dimensional modeling techniques. The composite space of the three-dimensional subject model 120 may correspond to an outer epidermal layer of the subject 115. The negative space of the three-dimensional subject model 120 may correspond to the empty space around the body of the subject 115. In some embodiments, the three-dimensional model may be a computer-aided design (CAD) model. The three-dimensional modeling techniques used by the image converter 230 may include polygonal modeling (e.g., polygon mesh and vector graphics, etc.) or curve modeling (e.g., splines and patches, etc.), among others.

In some embodiments, the image converter 230 may apply contour detection and/or image segmentation techniques in generating the three-dimensional subject model 120. If the image acquired by the imaging device 210 is an MRI scan or a CAT scan, the image converter 230 may identify an outer boundary at each scanned slice. In some embodiments, the image converter 230 may use an edge detection algorithm to detect the outer boundary at each scanned slice. The outer boundaries at each scanned slice may correspond to the outer epidermal layer of the subject 115. Using the outer boundaries, the image converter 230 may construct the three-dimensional model using the previously mentioned modeling techniques.

Figure 3A:
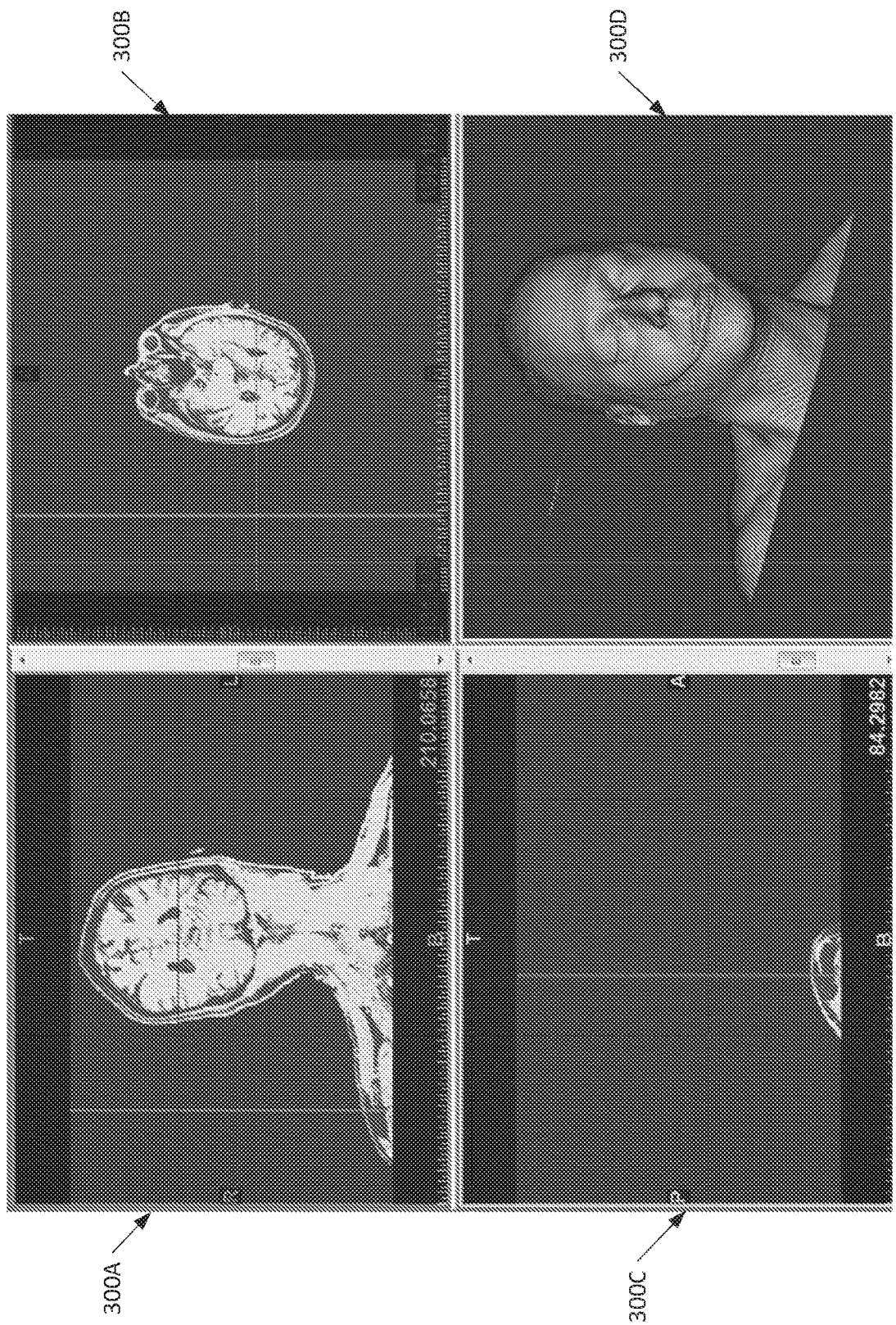
FIGS. 3A-3F are screenshots showing applications of various image processing techniques on a mold block model in processing immobilization molds, according to illustrative embodiments.

Referring now to FIG. 3A, depicted are screenshots 300A-300D showing an application of contour detection and image segmentation in generating the three-dimensional subject model 120. In the context of FIG. 2, the three-dimension image taken by the imaging device 210 may be an MRI scan. The MRI scan may include one or more slices, such as those in screenshots 300A-300C. For each of the slices (e.g., screenshots 300A-300C), the image converter 230 may identify the outer edge of the MRI of the subject 115 using contour detection techniques (e.g., edge detection). Using the identified outer edges, the image converter 230 may generate the three-dimension model of the subject 115 (e.g., screenshot 300D). The image converter 230 may apply image segmentation techniques, and may assign or label a portion of an entirety of the three dimensional model corresponding to the subject 115 as a single segment.

Using the generated three-dimensional subject model 120, the image converter 230 may apply additional image processing techniques in preparation of generating the three-dimensional mold block model 125. In some embodiments, the image converter 230 may export to another format for use in another application (e.g., SPACECLAIM or MAT-LAB). In some embodiments, the image converter 230 may identify a portion of the three-dimensional model 120 corresponding to the body of the subject 115. In some embodiments, the portion of the three-dimensional model 120 corresponding to the body of the subject 115 may be determined using edge detection. In some embodiments, the portion of the three-dimension model 120 corresponding to the body of the subject 115 may be determined based the labeling assigned using the image segmentation technique applied previously. In some embodiments, the image converter 230 may apply a filter (e.g. a smoothing filter) on the three-dimensional subject model 120 to reduce artefacts and rapid changes. In some embodiments, the image converter 230 may reorient the three-dimension subject model 120 to a specified axis. The specified axis may correspond to a direction in which the subject 115 will lie in the final manufactured immobilization mold 220.

Figure 3B:
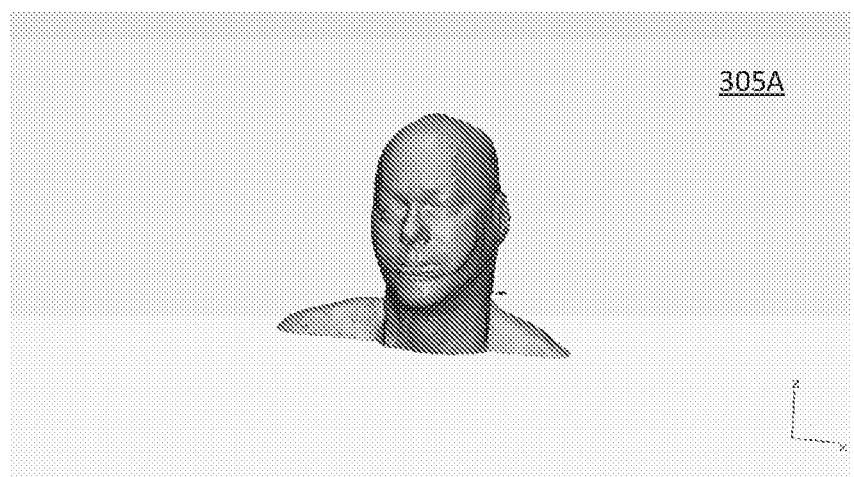
Figure 3C:
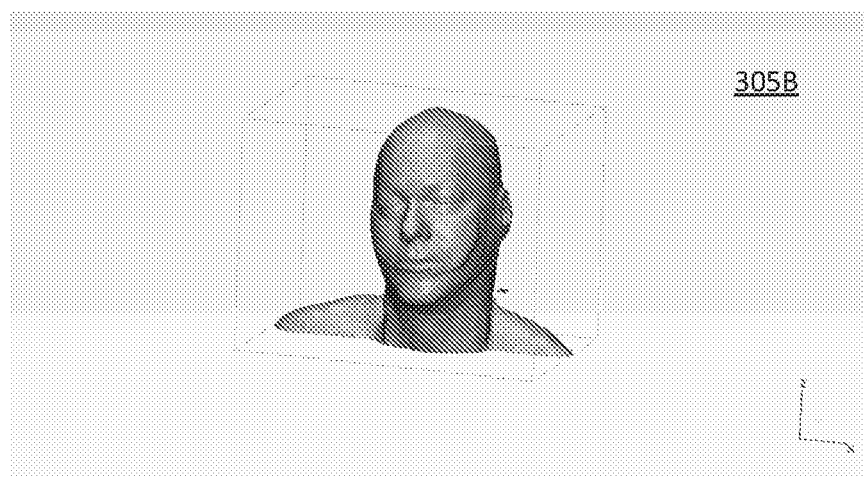
Figure 3D:
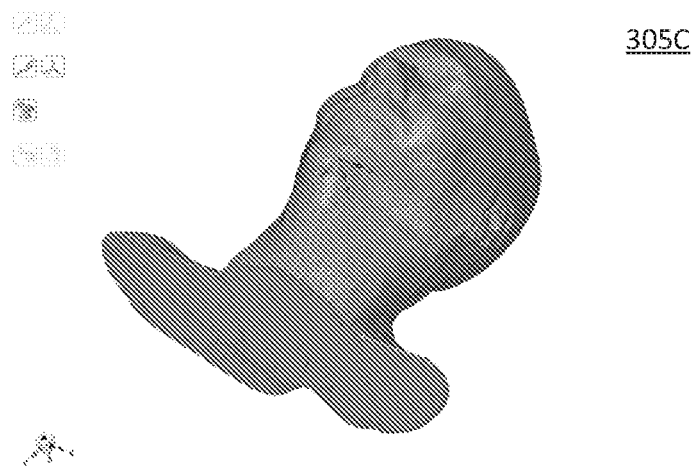

Referring now to FIGS. 3B-3D, depicted are screenshots 305A-305C showing an application of re-orientation on the three-dimensional subject model 120. In the context of FIG. 2, in screenshot 305A, the image converter 230 may receive the exported three-dimensional subject model 120. In screenshot 305B, the image converter 230 may identify the portion of the three-dimension model corresponding to the body of the subject 115. The image converter 230 may also apply a smoothing function to the three-dimensional subject model 120 (e.g., using a shrinkwrap function of SPACE-CLAIM). In screenshot 305C, the image converter 230 may reorient the axis of the three-dimensional subject model 120 of the body of the subject 115.

Using the three-dimensional model, the mold model generator 235 in turn may generate the mold block model 125 for the immobilization mold 220. To start, the mold model generator 235 may generate a generic block model. The generic block model may initially include all composite space. In some embodiments, generic block model may correspond to a raw block from which the imprint or cavity for the subject 115 will be milled. The mold model generator 235 may in turn combine the three-dimensional subject model 120 with the generic block model to generate the mold block model 125. In some embodiments, the mold model generator 235 may identify a side of the three-dimensional subject model 120. The side may correspond to the side of the body of the subject 115 toward or along the torso of the subject 115. In some embodiments, the mold model generator 235 may position or align the identified side of the three-dimensional subject model 120 with a side of the generic block model. Once positioned or aligned, the mold model generator 235 may subtract the composite portion of the three-dimensional subject model 120 from the generic block model. In some embodiments, the mold model generator 235 may perform a Boolean subtraction of the composite portion of the three-dimensional subject model 120 from the generic block model to generate the mold block model 125.

Figure 3E:
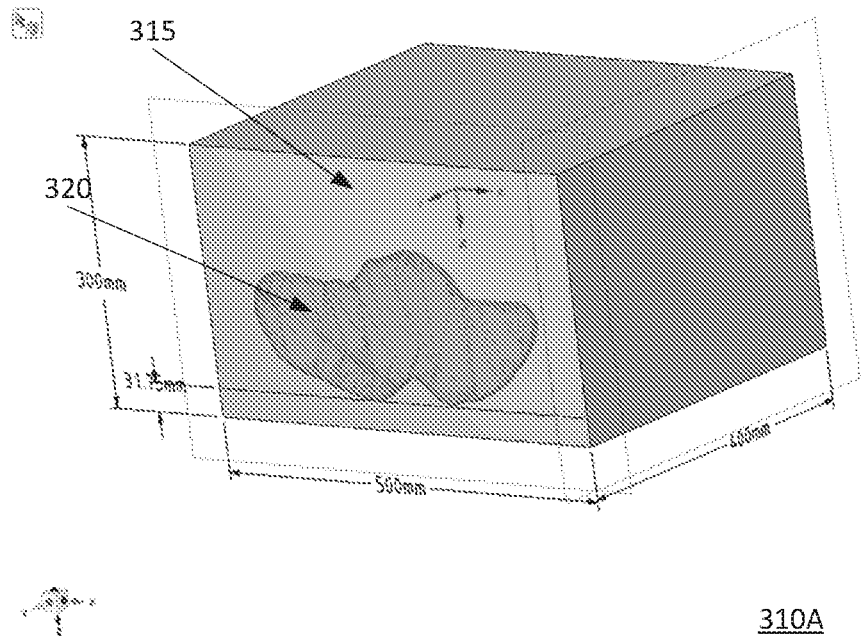
Figure 3F:
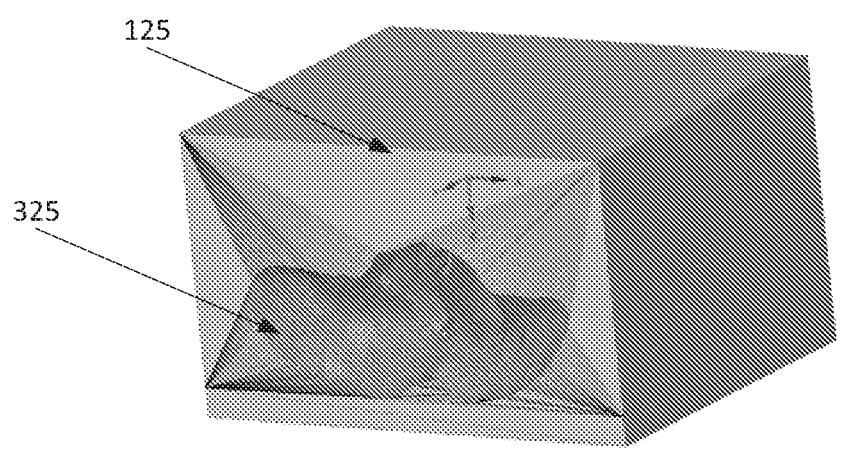

Referring now to FIGS. 3E and 3F, shown are screenshots 310A and 310B of a Boolean subtraction performed on the generic block model. In the context of FIG. 2, in screenshot 310A, the mold model generator 235 may position the three-dimensional model 320 of the subject 115 within the generic block model 315. The mold model generator 235 may align one side of the three-dimensional subject model 320 with the generic block model 315. In screenshot 310B, the mold model generator 235 may perform a Boolean subtraction of the three-dimensional subject model 320 from the generic block model 315 to generate the mold block model 125 with an opening 325 corresponding to negative space.

With the mold block model 125 generated, the mold model generator 235 may remove a portion of the mold block model 125 to expose the opening (e.g., opening 325 in FIG. 3F). The mold model generator 235 may traverse each two-dimensional slice of the mold block model 125 to remove the portion to expose the opening. In some embodiments, the traversal may be along one axis (e.g., x-axis or y-axis) or both axes (e.g., x-axis and then y-axis, or vice-versa). The mold model generator 235 may in addition remove other portions from the mold block model 125 to allow the subject 115 to enter into the resulting imprint or cavity in the immobilization mold 220.

At each two-dimensional slice, the mold model generator 235 may identify each opening. The opening may correspond to negative or empty space within the model block model 125. In some embodiments, the mold model generator 235 may identify one or more continuous portions of the three-dimensional model corresponding to the subject 115 (e.g., three-dimensional subject model 320) at each slice. For each contiguous portion or opening, the mold model generator 235 may identify a midline bisecting the contiguous portion or the opening to divide the contiguous portion or the opening into two congruent parts. The two portions may be substantially congruent in area, deviating 0% to 20% from each other in area. In some embodiments, the mold model generator 235 may partition the contiguous portion or the opening about the midline for processing the three-dimensional model or the opening in the mold block model 125 to generate a first half and a second half of the slice. The mold model generator 235 may then process the first half and the second half separately in removing the portion of the mold model block 125. In some embodiments, the mold model generator 235 may divide each contiguous portion or opening into multiple congruent or non-congruent portions to process separately.

Figure 4A:
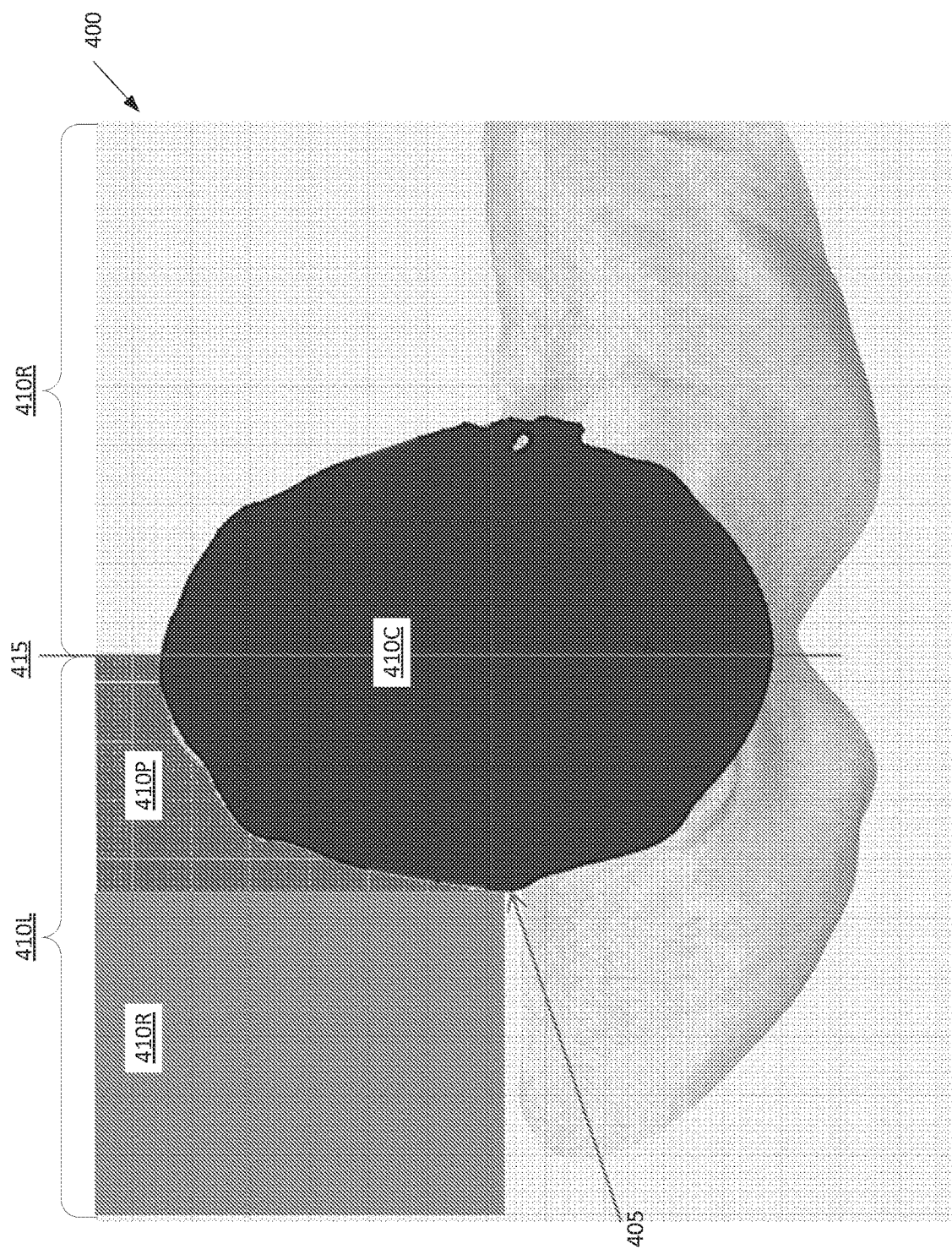
FIGS. 4A-4E are screenshots showing applications of mold optimization techniques on a mold block model in processing immobilization molds, according to an illustrative embodiments.

Referring now to FIGS. 4A-4E, depicted are screenshots showing the sequence of removing the portion of the mold block model 125 to expose the opening. Referring now to FIG. 4A, shown is one slice 400 of a three-dimensional subject generated by the image converter 230. The entirety of 400 may correspond to a layer or slice of a mold block model 125 and in turn may also correspond to a layer or slice of the to-be generated immobilization mold 220. The mold model generator 235 may identify the contiguous portion 410C corresponding to a portion of the body of the subject 115. The mold model generator 235 may identify a midline 415 along the contiguous portion 405 of the three-dimensional subject model. The mold model generator 235 may partition the slice 400 along the identified midline 415 to a left side 410L (corresponding to a left side of the subject 115) and a right side 410R (corresponding to a right side of the subject 115). The mold model generator 235 may then process the left side 410L and the right side 410R separately. As will be discussed below, the mold model generator 235 may process each side 410L and 410R from one end to another (e.g., top-down, bottom-up, left-to-right, right-to-left, etc.). On the left side 410L, the mold model generator 235 may identify point 405 as an extrema along the outer edge of the contiguous portion 410C corresponding to the body of the subject 115. The mold model generator 235 may remove the portion 410R above the point 405 and to left of the contiguous portion 410C. The mold model generator 235 may also remove portion 410P above the point 405 and above the contiguous portion 410C of the mold block model 125 to expose the opening or the contiguous portion 410C.

Figure 4B:
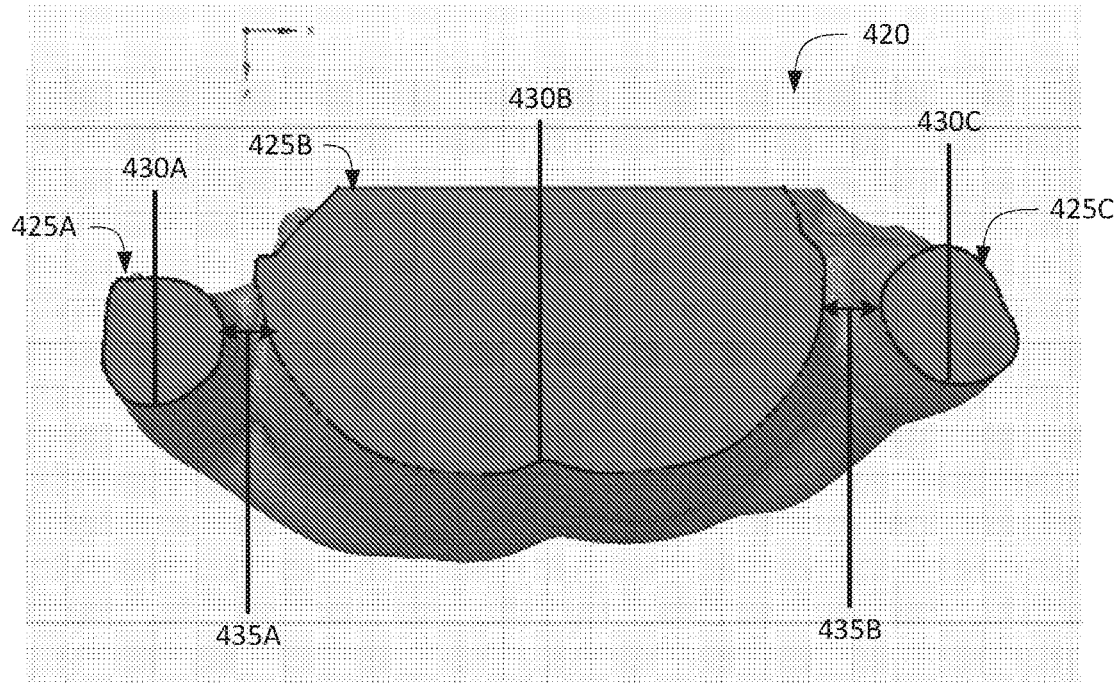
Figure 4C:
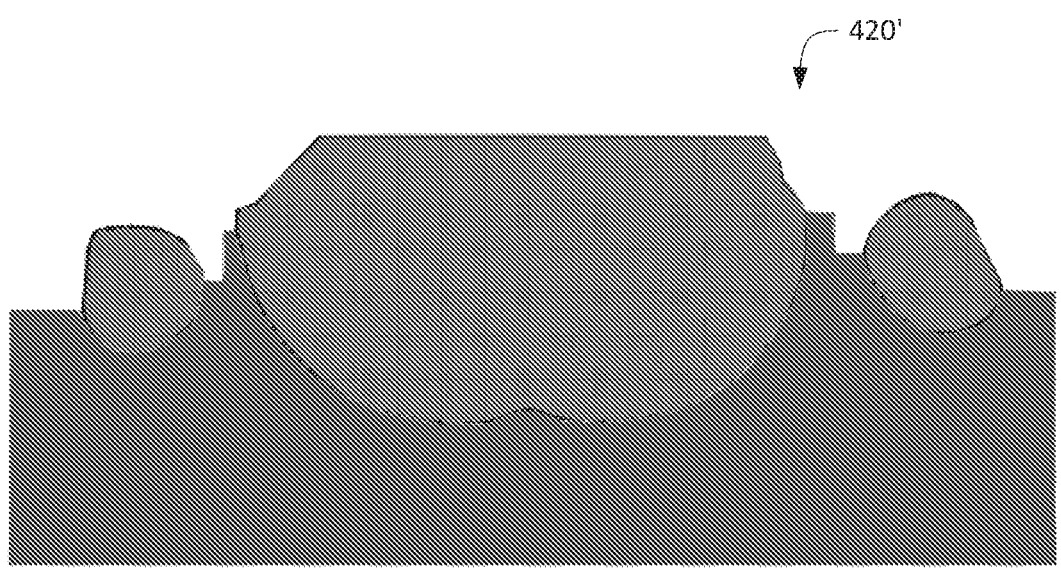

Referring now to FIGS. 4B and 4C, shown is one slice 420 of a three-dimensional subject model generated by the image converter 230. In the scenario depicted in FIGS. 4B and 4C, the slice 420 of the three-dimensional subject model may have multiple contiguous portions 425A-425C. The first portion 425A may correspond to a left arm of the subject 115. The second portion 425B may correspond to a torso of the subject 115. The third portion 425C may correspond to a right arm of the subject 115. The first portion 425A may be separated from the second portion 425B by a distance indicated by 435A. The second portion 425B may be separated from the third portion 425C by a distance indicated by 435B. For each contiguous portion 425A-425C, the mold model generator 235 may identify a respective midline 430A-430C bisecting the corresponding portion 425A-425C to divide into roughly congruent halves.

Returning back to FIG. 2, at each half for each slice, the mold model generator 235 may identify a global extremum and one or more local extrema of the opening in the mold block model 125 relative to the midline or a side of the slice opposite of the midline. In some embodiments, the mold model generator 235 may identify a global minimum and one or more local minima of the mold block model 125 relative to the side of the slice opposite of the midline. The global minimum may correspond to the maximum width-wise protrusion of the body surface of the subject 115 in the to-be generated mold 220. The one or more local minima may correspond to other width-wise protrusions of the body of the subject 115 in the to-be generated mold 220. In some embodiments, the mold model generator 235 may identify a global maximum and one or more local maxima of the mold block model 125 relative to the midline. The global maximum may correspond to the maximum width-wise protrusion of the body surface of the subject 115 in the to-be generated mold 220. The one or more local maxima may correspond to other width-wise protrusions of the body of the subject 115 in the to-be generated mold 220. In some embodiments, the mold model generator 235 may identify an initial point or terminal point of the opening in the mold block model 125 at each half of each slice. From the initial point or the terminal point, the mold model generator 235 may commence identification of the global extremum and the one or more local extrema.

With the global extremum and the one or more local extrema of each half of each slice identified, the mold model generator 235 may remove one or more portions of the mold block model 125. In some embodiments, the mold model generator 235 may select or identify a side in which the subject 115 is to enter the immobilization mold 220. The selection of the side of the immobilization mold 220 may be in accordance to the specified treatment. In some embodiments, the mold model generator 235 may remove the one or more portions of the mold block model 125 from the side in which the subject 115 is to enter. For each half of the slice, the mold model generator 235 may identify the global extremum (e.g., the global maximum or global minimum). Along the global extremum relative to a side perpendicular to identified midline, the mold model generator 235 may remove a portion of the mold block model 125 to expose the opening. The portion removed may correspond to an outer face of the mold block model 125 corresponding to the side of the to-be manufactured immobilization mold 220 in which the subject 115 will lie in. The mold model generator 235 may also identify a pair of local extrema (e.g., two local maxima or two local minima). In some embodiments, the mold model generator 235 may identify a pair of extrema including the global extrema and one of the local extremum. Using the pair of local extrema, the mold model generator 235 may remove the portion of the mold block model 125 between the pair of local extrema. In this manner, the subject 115 may not be prevented from entering into the imprint or cavity on the mold 220.

Figure 4D:
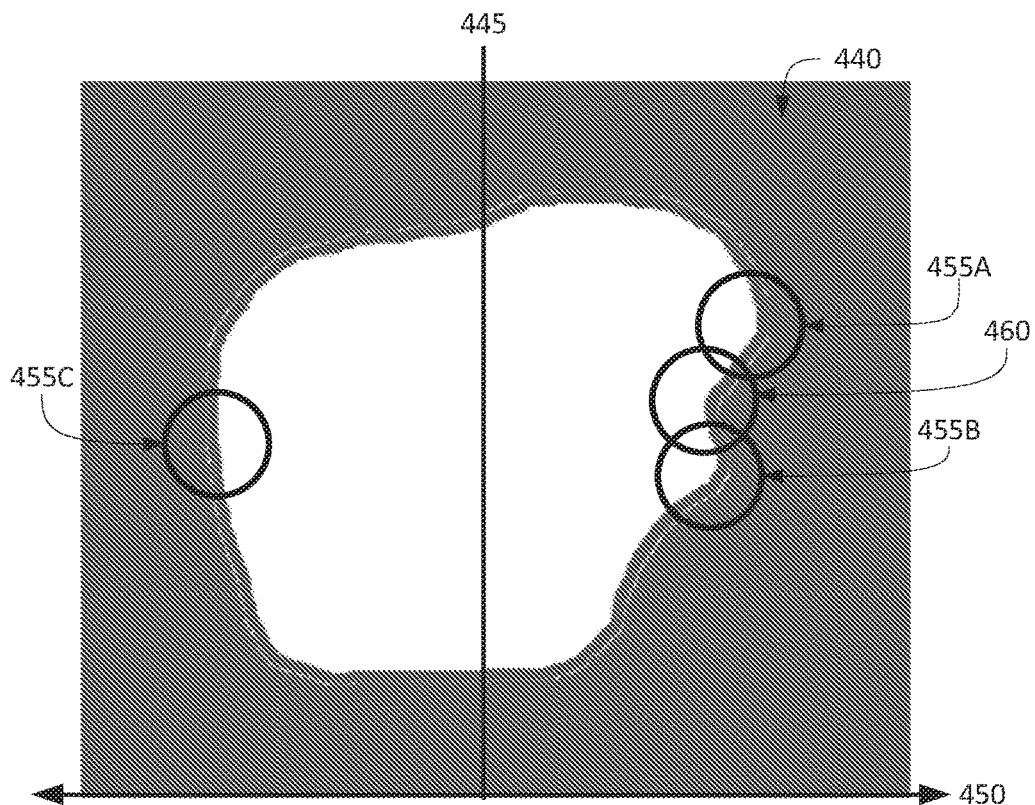
Figure 4E:
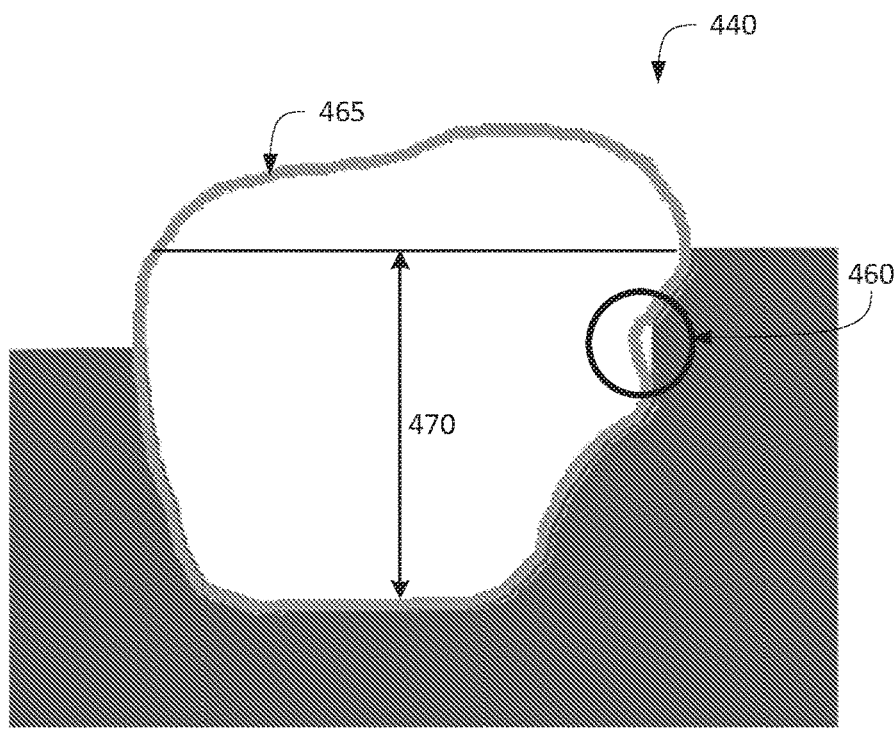

Referring now to FIGS. 4D and 4E, shown are block diagrams of the mold block model 440 with portions removed. Starting with FIG. 4D, in the context of FIG. 2, the mold model generator 235 may identify a slice 440 of the mold block model 125. The mold model generator 235 may identify a midline 445 that bisects the opening in the slice 440 into a left half and a right half. On each half, the mold model generator 235 may identify global extremum and one or more local extrema relative to the midline 445 along an axis 445. On the right half of the midline 445, the mold model generator 235 may identify a global extremum point 455A and a local extremum point 455B. On the left half of the midline 445, the mold model generator 235 may identify one global extreme point 455C. Moving onto FIG. 4E, the mold model generator 235 may remove a portion of the model mold 125 for the slice 440 above the global extremum point 455C on the left half of the slice 440 and above the global extremum point 455A on the right half of the slice 440 to expose the opening of the mold block model 125 to define an imprint 470. The mold model generator 235 may identify a portion 460 of the mold model 125 at the slice 440 extruding between the local extremum point 455A and global extremum point 455B on the right half of the slice 440. The portion 460 may itself be about a local extremum (e.g., a local maximum). Once identified, the mold model generator 235 may remove the portion 460 extruding between the pair of extrema 455A and 455B. In this manner, the immobilization mold 220 may lack any intermedial protrusions (e.g., portion 460) along the walls of the imprint 470, allowing a body 465 of the subject 115 to fully enter into the imprint 470 of the to-be manufactured immobilization mold 220 without being prevented by extruding portions.

Figure 5A:
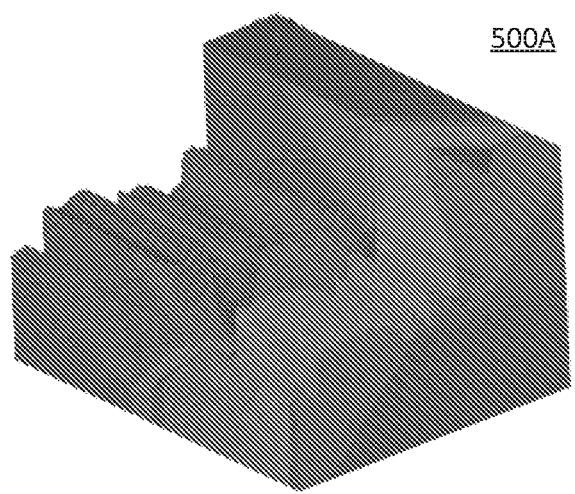
Figure 5B:
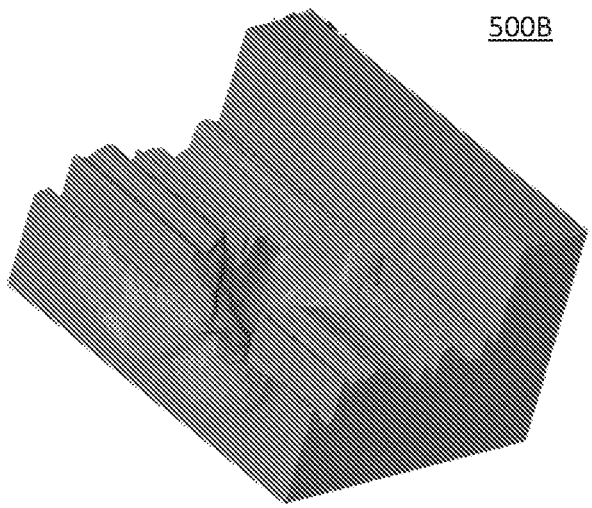
Figure 5C:
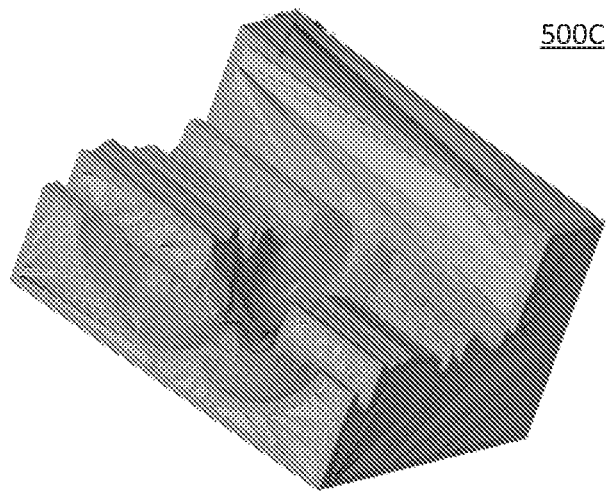

Subsequently, the mold model optimizer 240 may perform additional image processing techniques to the mold block model 125. Referring now to FIGS. 5A-5C, shown are screenshots 500A-500C showing applications of additional image processing techniques on mold block model 125. In some embodiments, the mold model optimizer 240 may add composite space to the mold block model 125 to make the mold block model 125 watertight (e.g., using the auto fix function in SPACECLAIM as in screenshot 500A of FIG. 5A). In some embodiments, the mold model optimizer 240 may apply a smoothing filter on the mold block model 125 (e.g., using wrap function set at 1 mm in SPACECLAIM as in screenshot 500B of FIG. 5B). In some embodiments, the mold model optimizer 240 may reduce a number of meshes or curves in modeling the mold block model 125 (e.g., using the reduce function of SPACECLAIM as in screenshot 500C of FIG. 5C). In some embodiments, the mold model optimizer 240 may increase or decrease the depth of the mold block model 125.

In some embodiments, the mold model optimizer 240 may identify a manufacturing modality of the mold generator 215. The manufacturing modality may be one of subtractive manufacturing (e.g., milling or grinding, etc.) or additive manufacturing (e.g., three-dimensional printing). Based on the manufacturing modality of the mold generator 215, the mold model optimizer 240 may further add or remove portions from the mold block model 125. If the manufacturing modality is subtractive manufacturing, the mold model optimizer 240 may maintain the generated mold block model 125 as is. If the manufacturing modality is additive manufacturing, the mold model optimizer 240 may remove one or more portions of the mold block model 125 that are not co-planar with at least a portion of the three-dimensional subject model 120 relative to the mold block model 125.

One or more accessories may be inserted, affixed, or otherwise added into the to-be generated mold 220. The one or more accessories may include one or more tensioners (e.g., straps) to restrain the subject 110, one or more anchoring mechanism (e.g., retention blocks) to help the to-be-generated mold 220 be affixed to the operating table, one or more sensors or probes, and one or more therapy application devices (e.g., for applying e.g., radiotherapy, sound therapy, magnetic therapy, mechanical therapy, electrotherapy, or temperature therapy, etc. on the subject 115), among others. To that end, the accessory positioner 245 may identify or set a position in the mold model block 120 for the each accessory. Each accessor may be defined in accordance to a schematic. The schematic may specify dimensions for the accessory and dimensions for an opening to hold, fit, or insert the accessory within the immobilization mold 220. In some embodiments, the schematic may specify addition of composition portions to hold the accessory into the immobilization mold 220. The schematics for the accessories may be stored and maintained on the immobilization mold creator system 205. The accessory position 245 may receive or identify a selection of one or more accessories to be included into the immobilization mold 220. The selection may include a position at which the accessory is to be included into the immobilization mold. The accessory positioner 245 may identify the schema corresponding to the selected accessory. The accessory positioner 245 may identify the dimensions for the accessory or the dimensions for the opening to insert the accessory from the schematic. Using the dimensions specified by the schematic for the accessory, the accessory positioner 245 may remove a portion in the mold block model 125 for inserting each accessory. In some embodiments, accessory positioner 245 may add a composite portion in the mold block model 125 for inserting the accessory. In some embodiments, the accessory positioner 245 may identify the composite portions to be added from the schematic for the accessory. The portion added or removed from the mold block model 125 may be configured to hold the accessory. In some embodiments, the accessory positioner 245 may determine the composite portions to be added based on the dimensions of the accessory. The portion added or removed from the mold block model 125 may correspond to the dimensions of the accessory.

With the mold block model 125 fully generated and modified, the mold generator 235 may send the mold block model 125 to the mold generator 215. The mold generator 215 may be an additive manufacturing device (e.g., three-dimensional printer) or a subtractive manufacturing device (e.g., miller or grinder device). In some embodiments, the mold generator 215 may be a three-dimensional printer device (e.g., extrusion deposition, granular material binding, lamination, photo-polymerization, or powder-fed directed energy deposition, etc.) to deposit material to form the immobilization mold 220. In some embodiments, if a three-dimensional printer device is used as the mold generator 215, the mold generator 215 may print an outline support (e.g., gridded support structure along the mesh or curves of the mold block model 125), rather than an imprint or cavity in a block. In some embodiments, if a three-dimensional printer device is used as the mold generator 215, the mold generator 215 may print a block with an imprint or cavity for the subject 115. In some embodiments, the mold generator 215 may be a milling machine using computer numerical control (CNC) techniques to remove material from a block of material to form the immobilization mold 220. In some embodiments, the mold generator 215 may be a grinding device using an abrasive tool (e.g., grinding wheel) to remove material from a block of material to form the immobilization mold 220. The material used to manufacture the immobilization mold 220 may have specific physical properties, such as a set ductility, plasticity, viscosity, elasticity, strain, strength, toughness, and viscoelasticity, among others. In some embodiments, the material used to manufacture the immobilization mold 220 may be hard matter (e.g., ceramics, metals, etc.) to hold the subject 115. The material used to manufacture the immobilization mold 220 may have a specific radiodensity, such as a set rate for radiolucency, radio-transparency, or radiopaqueness, among others. In some embodiments, the material can be selected based on the medical procedure for which the mold is being used. For instance, the mold may be made from a radiopaque material to block certain radiations if so desired. Alternatively, the mold may be made from a radiotranslucent material to allow radiation to pass through the mold. In addition, the material may be one that can be milled using conventional CNC milling machines. In the case of 3D printing, the material may be one can be used to deposit layers for producing a 3D printed mold. In addition, the material may allow for compression to provide comfort to the subject but still be firm enough to restrain movement of the subject, or immobilize the subject.

Figure 6A:
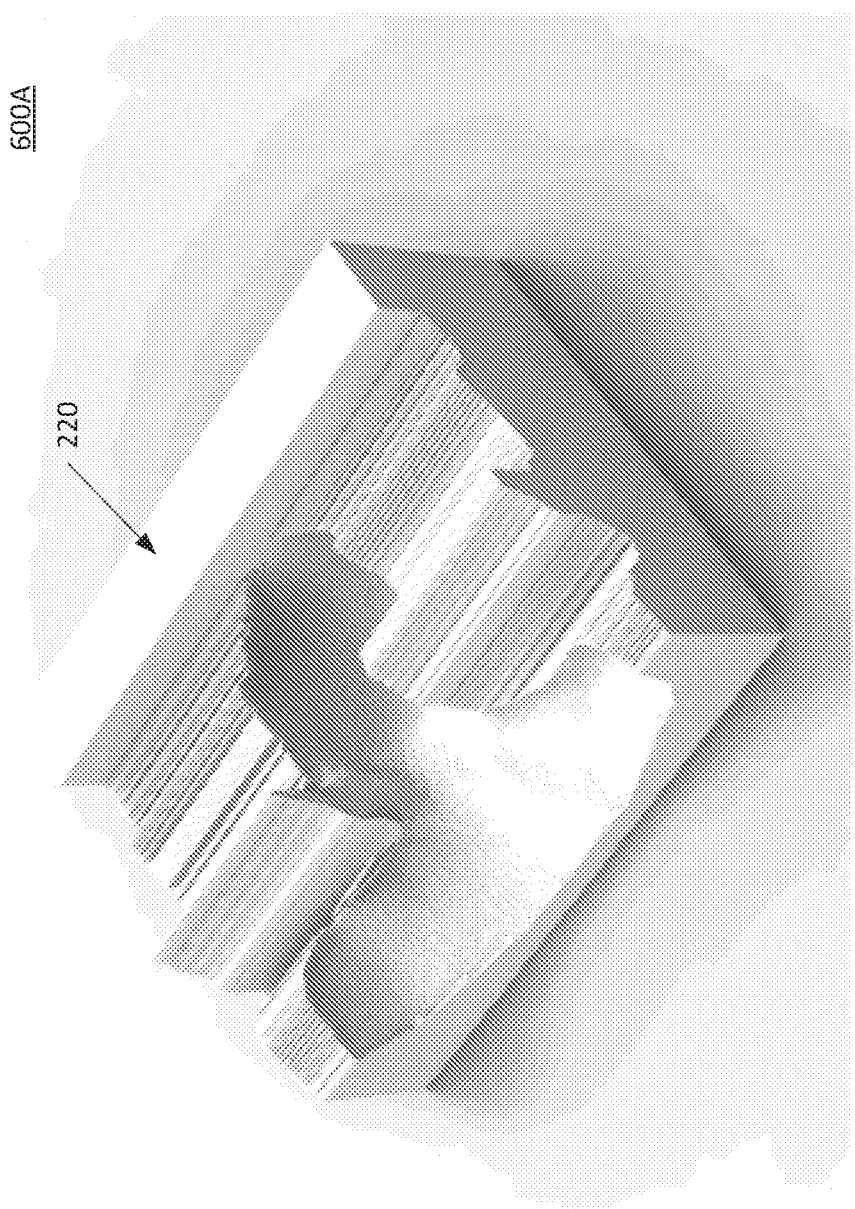
FIGS. 6A and 6B are screenshots showing a manufactured mold, according to an illustrative embodiment.
Figure 6B:
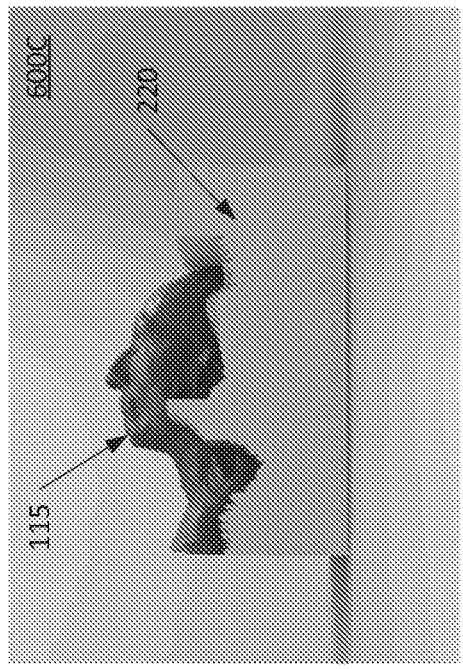
Figure 6B:
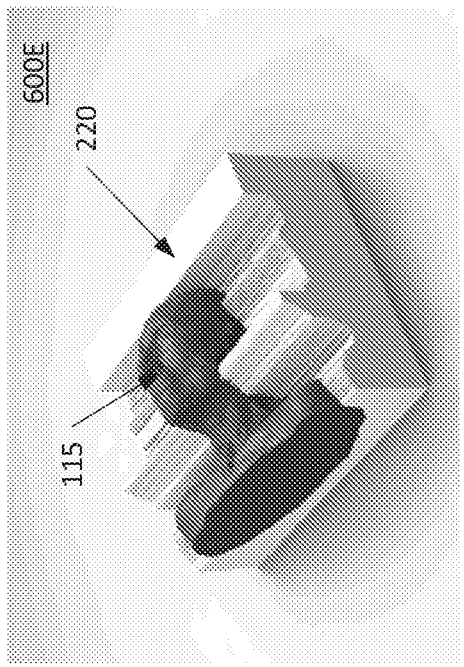
Figure 6B:
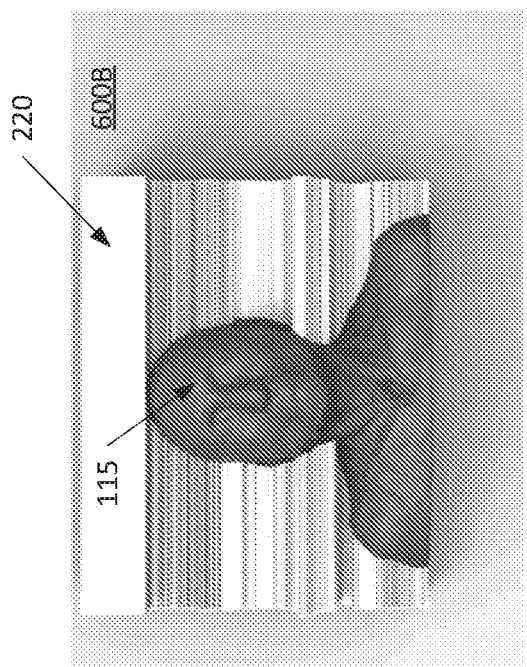
Figure 6B:
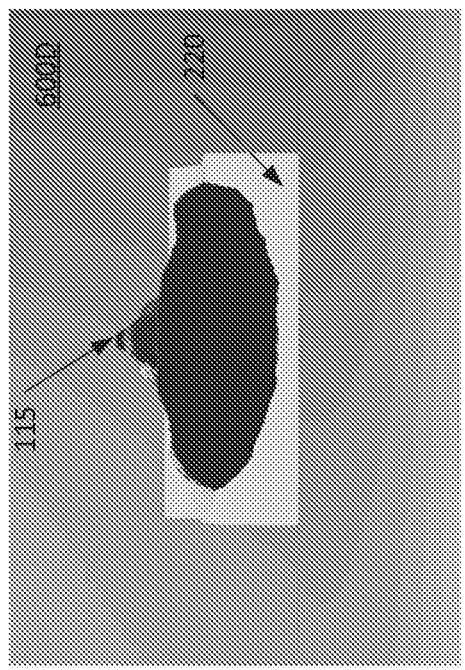

Referring now to FIGS. 6A and 6B, shown are screenshots 600A-600E of the finalized immobilization mold 220 manufactured by the mold generator 215. Starting with FIG. 6A, the shown immobilization mold 220 may include an imprint or cavity in the shape of the patient 115 cut to the depth of the global extremum at each layer and with any undercuts corresponding to a portion between a pair of extrema removed. In FIG. 6B, depicted is the placement of the patient 115 within the immobilization mold 220 from various angles. As illustrated, the patient 115 may be placed fixed and stationary within the immobilization mold 220. In this manner, the therapy (e.g., radiotherapy, heat therapy, electromagnetic therapy, magnetic therapy, sound therapy, etc.) may be assured to be applied and localized to the designated spot along the body of the patient 115.

Figure 6C:
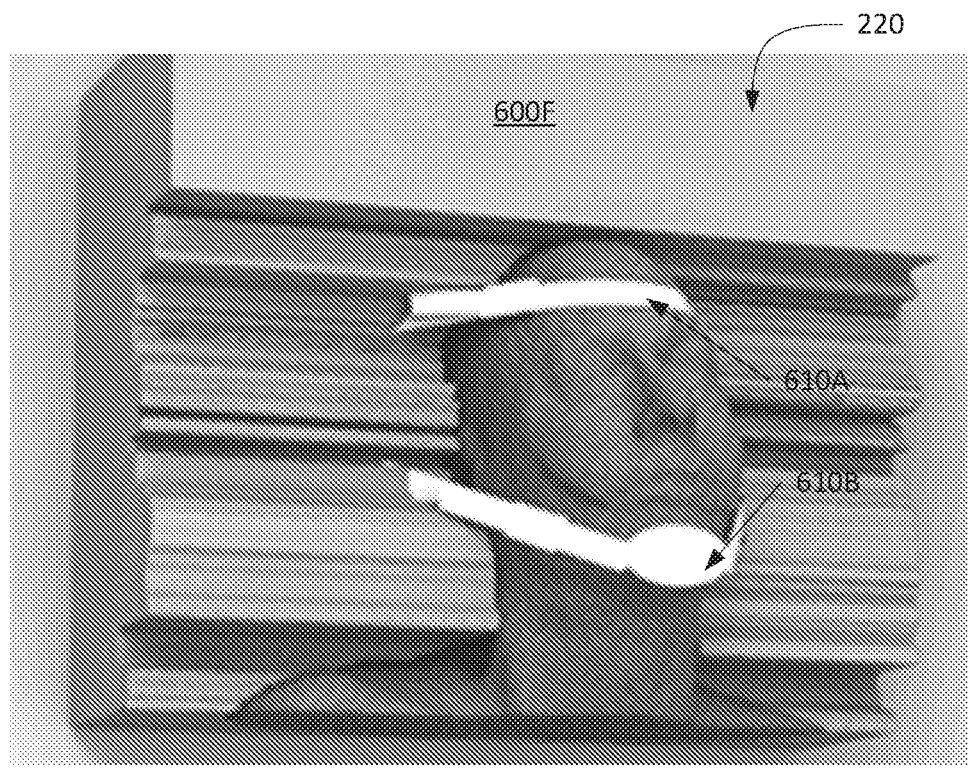
FIGS. 6C and 6D are screenshots showing a mold with additional accessories thereon, according to an illustrative embodiment.
Figure 6D:
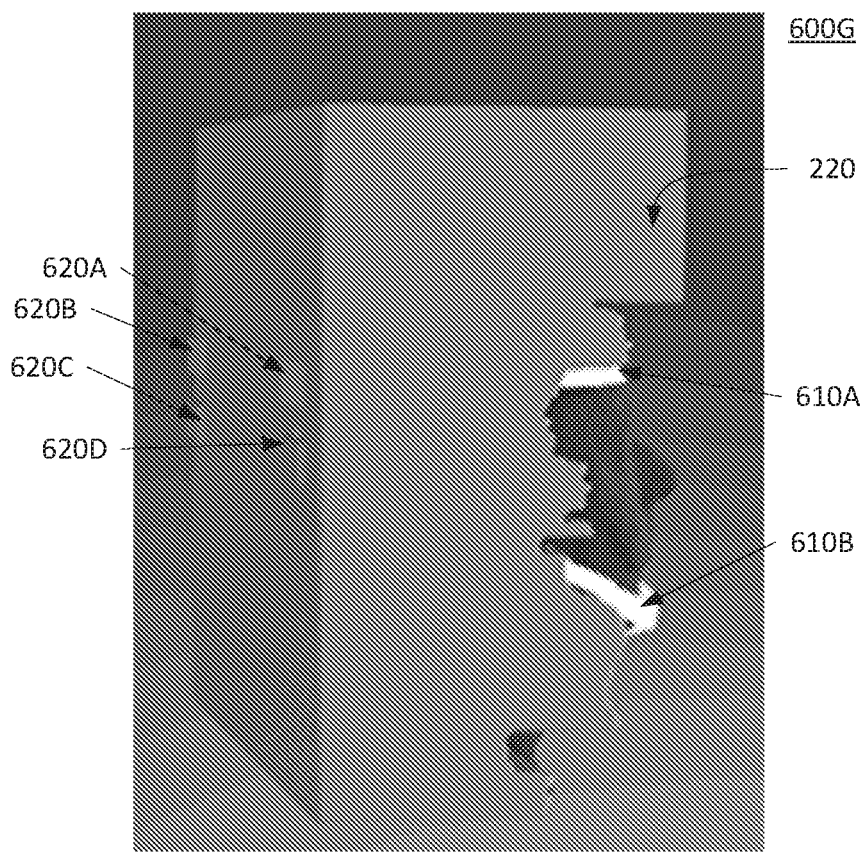

Subsequent to generating the immobilization mold 220, the one or more accessories may be added to the mold 220 by the mold generator 215 or another device. Referring now to FIGS. 6C and 6D, shown are screenshots 600F and 600G showing the immobilization mold 220 with additional accessories thereon. In FIG. 6C, accessories may be inserted into the mold 220 to include two tensioners, such as a forehead strap 610A and a chin strap 610B. In FIG. 6D, additional accessories may be added to the mold 220 to include four retention blocks 620A-620D.

Figure 7A:
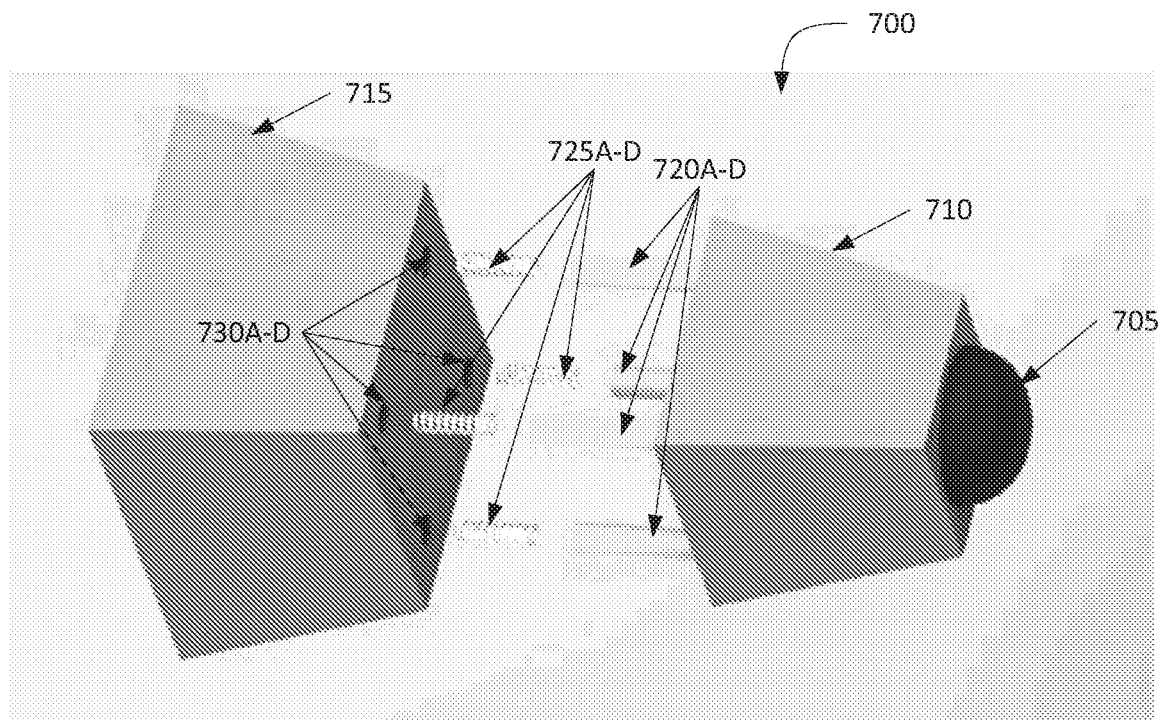
FIGS. 7A-7D are block diagrams depicting a sequence of inserting a probe into the mold, according to an illustrative embodiment.
Figure 7B:
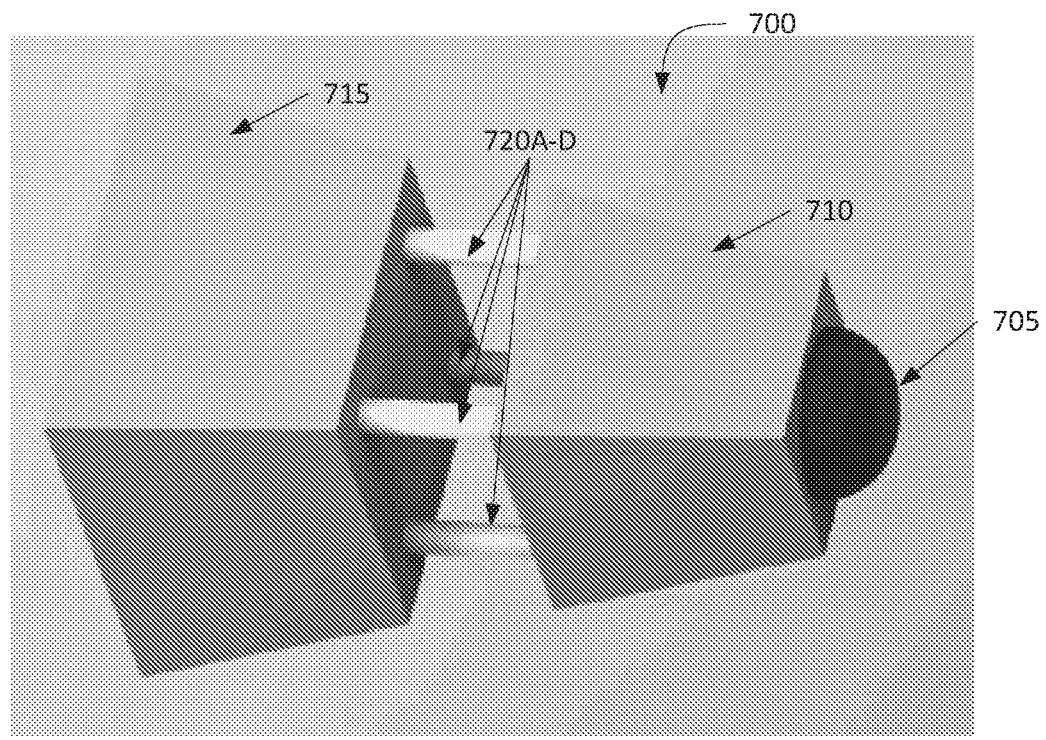

Referring now to FIGS. 7A-7D, shown are block diagrams depicting a sequence of inserting a probe 700 (e.g., ultrasound probe) into the mold 220. As seen in FIG. 7A, the probe 700 may include a sensory aperture 705, a first block 710, a second block 715, a set of extrusion legs 720A-720D, a set of biasing elements 725A-725D, and a set of support holes 730A-730D. The first block 710 may include a sensory aperture 705. The sensory aperture 705 may be one end of a sensor intended to be indirect contact with the subject 115 while lying in the imprint or cavity of the mold 220. The second block 715 may include additional sensor components, such as an input/output interface configured to be connected to another device. The biasing elements 725A-725D may include a spring mechanism (e.g., tension/extension, compression, torsion, variable spring) to allow for flexibility in addition to adherence between the first block 710 and the second block 715. The biasing elements 725A-725D may be placed such that the elements 725A-725 extend from the extrusion legs 720A-720D into the support holes 730A-730D. Each component of the probe 700 may be assembled or joined as seen in FIG. 7B.

Figure 7C:
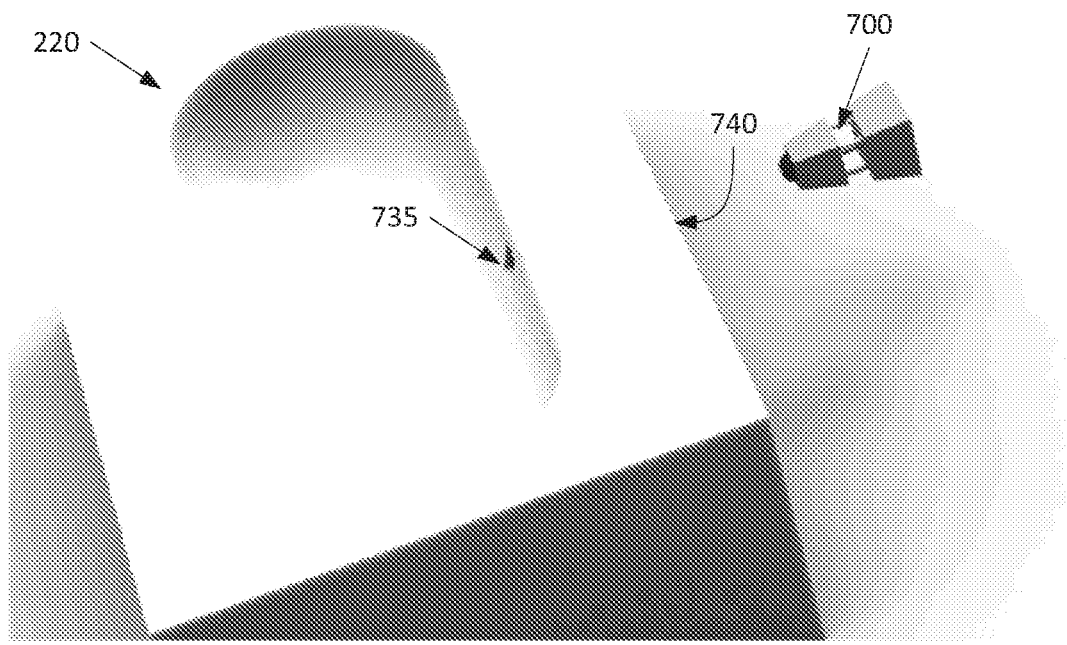
Figure 7D:
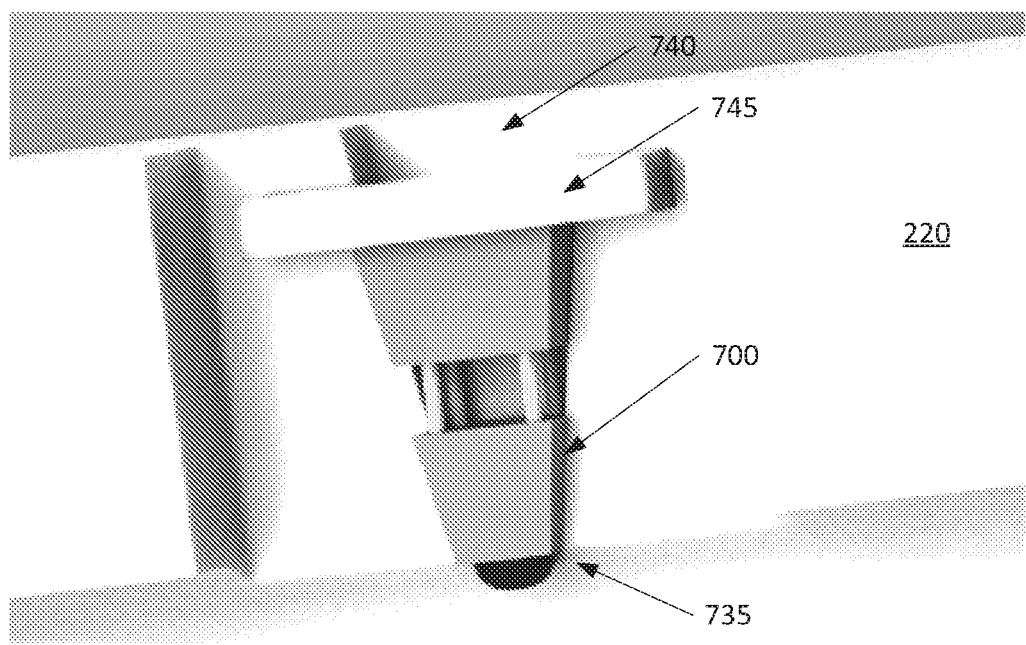

Once assembled, the probe 700 may be inserted into the mold 220 in the manner shown in FIGS. 7C and 7D. An opening may have been made by the mold generator 215 or another device into the immobilization mold 220 to form a contact end 735 and an insertion end 740. The probe 700 may be inserted into the insertion end 740, and may be capped with a capping element 745. The sensory aperture 705 may be exposed through the contact end 735. When the subject 115 lies into the imprint or cavity of the mold 220, the sensory aperture 705 may be in contact with the subject 115. Once inserted and operational, data gathered from the probe 700 may be used to adjust the application of the therapy onto the subject 115 (e.g., increase, decrease, or terminate dosage). The data may be used to also modify future manufacturing of the molds for the subject 115. In this manner, the sensory aperture 705 of the probe 700 may be placed in contact with the outer surface of the body of the subject 115. Additionally, the biasing elements 725A-725D may allow for the sensory aperture 705 to be in constant contact with the outer surface of the body of the subject 115, as the outer surface contracts or expands with the breathing of the subject 115. Furthermore, as the probe 700 may be situated within the mold 220 and enclosed by a capping element 745 (e.g., as shown in FIGS. 7C and 7D), the probe 700 may be remain relative stationary or secure.

Figure 8:
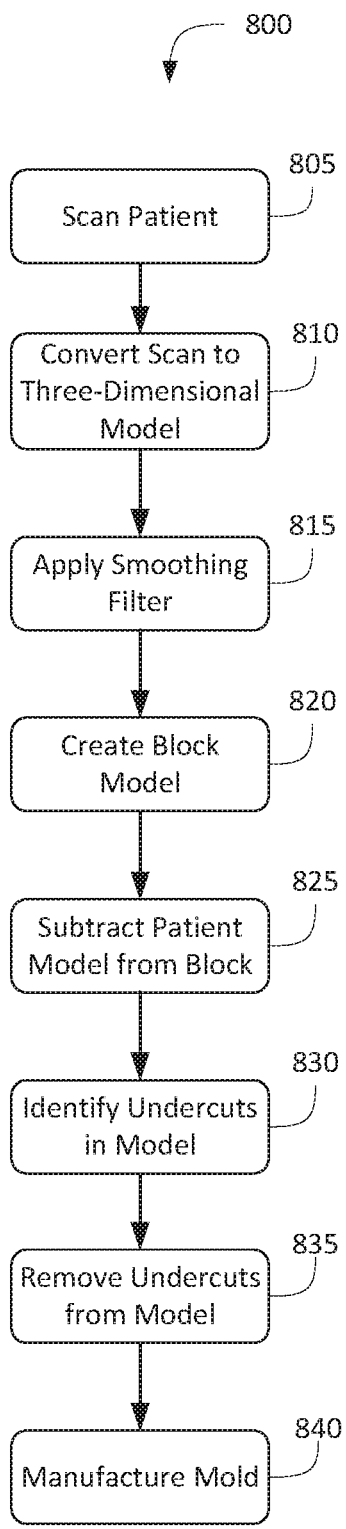
FIG. 8 is a flow diagram depicting a method of processing immobilization molds, according to an illustrative embodiment.

Referring now to FIG. 8, depicted is a method 800 of processing immobilization molds, according to an illustrative embodiment. The functionalities of method 800 may be performed by the immobilization mold creator system 200 as detailed in conjunction with FIG. 2 or the computing system 900 described in conjunction with FIGS. 9A-9D. In brief overview, at step 805, the computing device may scan a subject. At step 810, the computing device may perform contour detection and image segmentation to generate a three-dimensional model. At step 815, the computing device may apply a smoothing filter onto the three-dimensional model. At step 820, the computing device may create a generic block model. At step 825, the computing device may subtract the three-dimensional model of the subject from the generic block model. At step 830, the computing device may identify undercuts in an opening in the block model. At step 835, the computing device may remove the identified undercuts in the opening in the block model. At step 840, the computing device may manufacture an immobilization mold based on the block model using milling or three-dimensional printing.

B. Computing and Network Environment

Figure 9A:
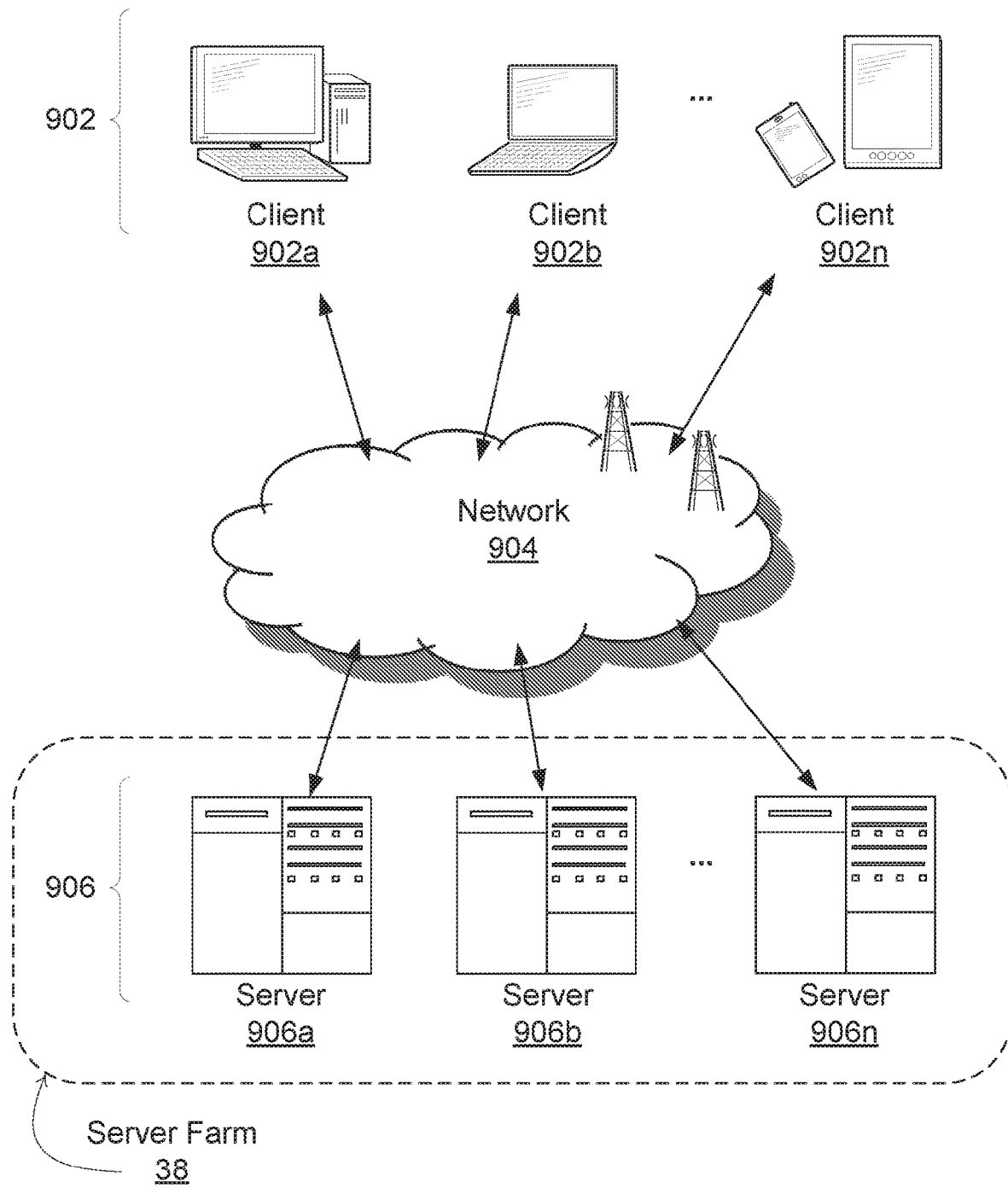
FIG. 9A is a block diagram depicting an embodiment of a network environment comprising client devices in communication with server devices.

It may be helpful to describe aspects of the operating environment as well as associated system components (e.g., hardware elements) in connection with the methods and systems described herein. Referring to FIG. 9A, an embodiment of a network environment is depicted. In brief overview, the illustrated exploring network environment includes one or more clients 902a-902n (also generally referred to as local machine(s) 902, client(s) 902, client node(s) 902, client machine(s) 902, client computer(s) 902, client device(s) 902, endpoint(s) 902, or endpoint node(s) 902) in communication with one or more servers 906a-906n (also generally referred to as server(s) 906, node 906, or remote machine(s) 906) via one or more networks 904. In some embodiments, a client 902 has the capacity to function as both a client node seeking access to resources provided by a server and as a server providing access to hosted resources for other clients 902a-902n.

Although FIG. 9A shows a network 904 between the clients 902 and the servers 906, the clients 902 and the servers 906 may be on the same network 904. In some embodiments, there are multiple networks 904 between the clients 902 and the servers 906. In one of these embodiments, a network 904' (not shown) may be a private network and a network 904 may be a public network. In another of these embodiments, a network 904 may be a private network and a network 904' a public network. In still another of these embodiments, networks 904 and 904' may both be private networks.

The network 904 may be connected via wired or wireless links. Wired links may include Digital Subscriber Line (DSL), coaxial cable lines, or optical fiber lines. The wireless links may include BLUETOOTH, Wi-Fi, NFC, RFID Worldwide Interoperability for Microwave Access (WiMAX), an infrared channel or satellite band. The wireless links may also include any cellular network standards used to communicate among mobile devices, including standards that qualify as 1G, 2G, 3G, or 4G. The network standards may qualify as one or more generation of mobile telecommunication standards by fulfilling a specification or standards such as the specifications maintained by International Telecommunication Union. The 3G standards, for example, may correspond to the International Mobile Telecommunications-2000 (IMT-2000) specification, and the 4G standards may correspond to the International Mobile Telecommunications Advanced (IMT-Advanced) specification. Examples of cellular network standards include AMPS, GSM, GPRS, UMTS, LTE, LTE Advanced, Mobile WiMAX, and WiMAX-Advanced. Cellular network standards may use various channel access methods e.g. FDMA, TDMA, CDMA, or SDMA. In some embodiments, different types of data may be transmitted via different links and standards. In other embodiments, the same types of data may be transmitted via different links and standards.

The network 904 may be any type and/or form of network. The geographical scope of the network 904 may vary widely and the network 904 can be a body area network (BAN), a personal area network (PAN), a local-area network (LAN), e.g. Intranet, a metropolitan area network (MAN), a wide area network (WAN), or the Internet. The topology of the network 904 may be of any form and may include, e.g., any of the following: point-to-point, bus, star, ring, mesh, or tree. The network 904 may be an overlay network, which is virtual and sits on top of one or more layers of other networks 904'. The network 904 may be of any such network topology as known to those ordinarily skilled in the art capable of supporting the operations described herein. The network 904 may utilize different techniques and layers or stacks of protocols, including, e.g., the Ethernet protocol, the internet protocol suite (TCP/IP), the ATM (Asynchronous Transfer Mode) technique, the SONET (Synchronous Optical Networking) protocol, or the SDH (Synchronous Digital Hierarchy) protocol. The TCP/IP internet protocol suite may include application layer, transport layer, internet layer (including, e.g., IPv6), or the link layer. The network 904 may be a type of a broadcast network, a telecommunications network, a data communication network, or a computer network.

In some embodiments, the system may include multiple, logically-grouped servers 906. In one of these embodiments, the logical group of servers may be referred to as a server farm 38 or a machine farm 38. In another of these embodiments, the servers 906 may be geographically dispersed. In other embodiments, a machine farm 38 may be administered as a single entity. In still other embodiments, the machine farm 38 includes a plurality of machine farms 38. The servers 906 within each machine farm 38 can be heterogeneous—one or more of the servers 906 or machines 906 can operate according to one type of operating system platform (e.g., WINDOWS NT, manufactured by Microsoft Corp. of Redmond, Wash.), while one or more of the other servers 906 can operate on according to another type of operating system platform (e.g., Unix, Linux, or Mac OS X).

In one embodiment, servers 906 in the machine farm 38 may be stored in high-density rack systems, along with associated storage systems, and located in an enterprise data center. In this embodiment, consolidating the servers 906 in this way may improve system manageability, data security, the physical security of the system, and system performance by locating servers 906 and high performance storage systems on localized high performance networks. Centralizing the servers 906 and storage systems and coupling them with advanced system management tools allows more efficient use of server resources.

The servers 906 of each machine farm 38 do not need to be physically proximate to another server 906 in the same machine farm 38. Thus, the group of servers 906 logically grouped as a machine farm 38 may be interconnected using a wide-area network (WAN) connection or a metropolitan-area network (MAN) connection. For example, a machine farm 38 may include servers 906 physically located in different continents or different regions of a continent, country, state, city, campus, or room. Data transmission speeds between servers 906 in the machine farm 38 can be increased if the servers 906 are connected using a local-area network (LAN) connection or some form of direct connection. Additionally, a heterogeneous machine farm 38 may include one or more servers 906 operating according to a type of operating system, while one or more other servers 906 execute one or more types of hypervisors rather than operating systems. In these embodiments, hypervisors may be used to emulate virtual hardware, partition physical hardware, virtualized physical hardware, and execute virtual machines that provide access to computing environments, allowing multiple operating systems to run concurrently on a host computer. Native hypervisors may run directly on the host computer. Hypervisors may include VMware ESX/ESXi, manufactured by VMWare, Inc., of Palo Alto, Calif.; the Xen hypervisor, an open source product whose development is overseen by Citrix Systems, Inc.; the HYPER-V hypervisors provided by Microsoft or others. Hosted hypervisors may run within an operating system on a second software level. Examples of hosted hypervisors may include VMware Workstation and VIRTUALBOX.

Management of the machine farm 38 may be de-centralized. For example, one or more servers 906 may comprise components, subsystems and modules to support one or more management services for the machine farm 38. In one of these embodiments, one or more servers 906 provide functionality for management of dynamic data, including techniques for handling failover, data replication, and increasing the robustness of the machine farm 38. Each server 906 may communicate with a persistent store and, in some embodiments, with a dynamic store.

Server 906 may be a file server, application server, web server, proxy server, appliance, network appliance, gateway, gateway server, virtualization server, deployment server, SSL VPN server, or firewall. In one embodiment, the server 906 may be referred to as a remote machine or a node. In another embodiment, a plurality of nodes 290 may be in the path between any two communicating servers.

Figure 9B:
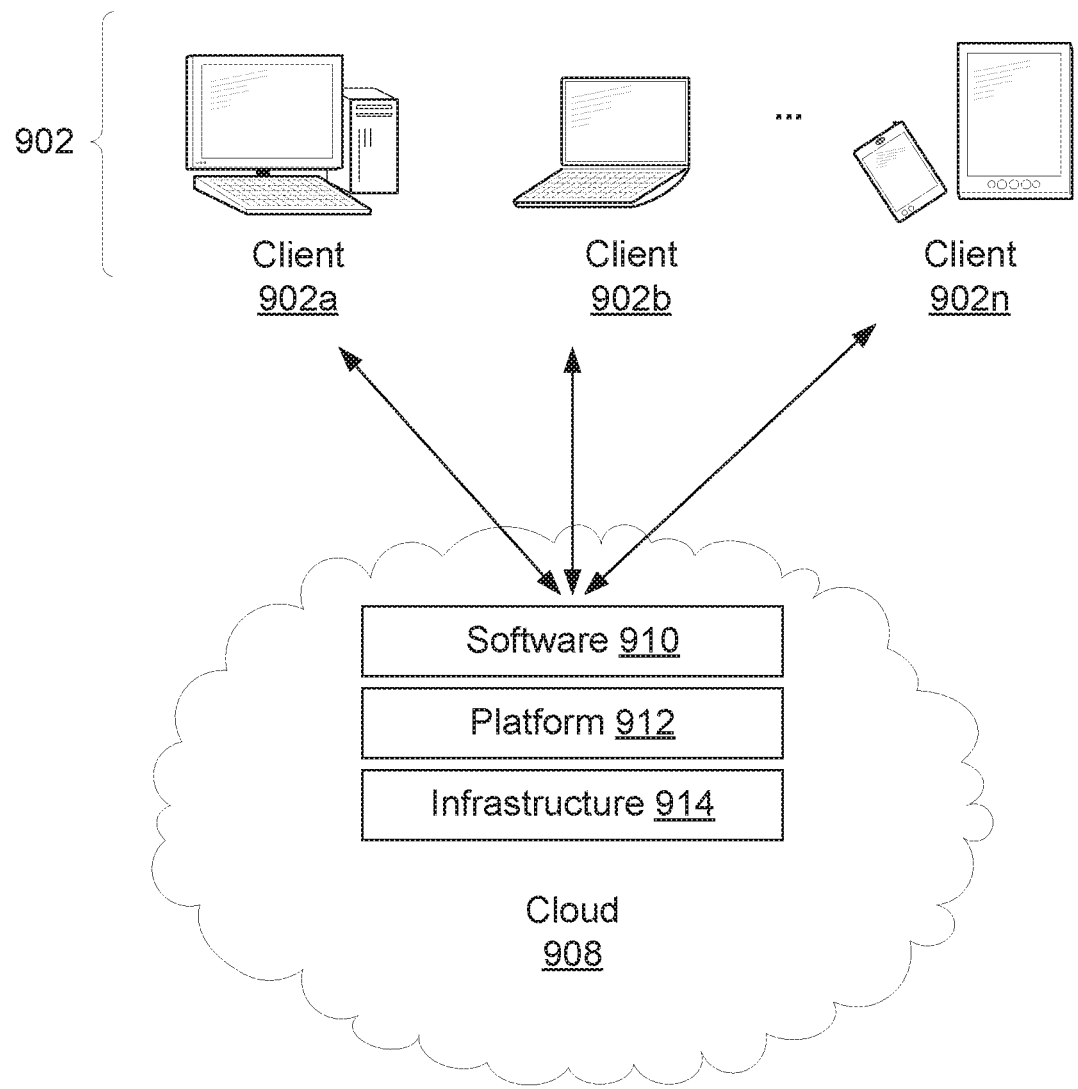
FIG. 9B is a block diagram depicting a cloud computing environment comprising client devices in communication with a cloud service provider.

Referring to FIG. 9B, a cloud computing environment is depicted. A cloud computing environment may provide client 902 with one or more resources provided by a network environment. The cloud computing environment may include one or more clients 902a-902n, in communication with the cloud 908 over one or more networks 904. Clients 902 may include, e.g., thick clients, thin clients, and zero clients. A thick client may provide at least some functionality even when disconnected from the cloud 908 or servers 906. A thin client or a zero client may depend on the connection to the cloud 908 or server 906 to provide functionality. A zero client may depend on the cloud 908 or other networks 904 or servers 906 to retrieve operating system data for the client device. The cloud 908 may include back end platforms, e.g., servers 906, storage, server farms or data centers.

The cloud 908 may be public, private, or hybrid. Public clouds may include public servers 906 that are maintained by third parties to the clients 902 or the owners of the clients. The servers 906 may be located off-site in remote geographical locations as disclosed above or otherwise. Public clouds may be connected to the servers 906 over a public network. Private clouds may include private servers 906 that are physically maintained by clients 902 or owners of clients. Private clouds may be connected to the servers 906 over a private network 904. Hybrid clouds 908 may include both the private and public networks 904 and servers 906.

The cloud 908 may also include a cloud based delivery, e.g. Software as a Service (SaaS) 910, Platform as a Service (PaaS) 912, and Infrastructure as a Service (IaaS) 914. IaaS may refer to a user renting the use of infrastructure resources that are needed during a specified time period. IaaS providers may offer storage, networking, servers or virtualization resources from large pools, allowing the users to quickly scale up by accessing more resources as needed. Examples of IaaS include AMAZON WEB SERVICES provided by Amazon.com, Inc., of Seattle, Wash., RACKSPACE CLOUD provided by Rackspace US, Inc., of San Antonio, Tex., Google Compute Engine provided by Google Inc. of Mountain View, Calif., or RIGHTSCALE provided by RightScale, Inc., of Santa Barbara, Calif. PaaS providers may offer functionality provided by IaaS, including, e.g., storage, networking, servers or virtualization, as well as additional resources such as, e.g., the operating system, middleware, or runtime resources. Examples of PaaS include WINDOWS AZURE provided by Microsoft Corporation of Redmond, Wash., Google App Engine provided by Google Inc., and HEROKU provided by Heroku, Inc. of San Francisco, Calif. SaaS providers may offer the resources that PaaS provides, including storage, networking, servers, virtualization, operating system, middleware, or runtime resources. In some embodiments, SaaS providers may offer additional resources including, e.g., data and application resources. Examples of SaaS include GOOGLE APPS provided by Google Inc., SALESFORCE provided by Salesforce.com Inc. of San Francisco, Calif., or OFFICE 365 provided by Microsoft Corporation. Examples of SaaS may also include data storage providers, e.g. DROPBOX provided by Dropbox, Inc. of San Francisco, Calif., Microsoft SKYDRIVE provided by Microsoft Corporation, Google Drive provided by Google Inc., or Apple ICLOUD provided by Apple Inc. of Cupertino, Calif.

Clients 902 may access IaaS resources with one or more IaaS standards, including, e.g., Amazon Elastic Compute Cloud (EC2), Open Cloud Computing Interface (OCCI), Cloud Infrastructure Management Interface (CIMI), or OpenStack standards. Some IaaS standards may allow clients access to resources over HTTP, and may use Representational State Transfer (REST) protocol or Simple Object Access Protocol (SOAP). Clients 902 may access PaaS resources with different PaaS interfaces. Some PaaS interfaces use HTTP packages, standard Java APIs, JavaMail API, Java Data Objects (JDO), Java Persistence API (JPA), Python APIs, web integration APIs for different programming languages including, e.g., Rack for Ruby, WSGI for Python, or PSGI for Perl, or other APIs that may be built on REST, HTTP, XML, or other protocols. Clients 902 may access SaaS resources through the use of web-based user interfaces, provided by a web browser (e.g. GOOGLE CHROME, Microsoft INTERNET EXPLORER, or Mozilla Firefox provided by Mozilla Foundation of Mountain View, Calif.). Clients 902 may also access SaaS resources through smartphone or tablet applications, including, e.g., Salesforce Sales Cloud, or Google Drive app. Clients 902 may also access SaaS resources through the client operating system, including, e.g., Windows file system for DROPBOX.

In some embodiments, access to IaaS, PaaS, or SaaS resources may be authenticated. For example, a server or authentication server may authenticate a user via security certificates, HTTPS, or API keys. API keys may include various encryption standards such as, e.g., Advanced Encryption Standard (AES). Data resources may be sent over Transport Layer Security (TLS) or Secure Sockets Layer (SSL).

Figure 9C:
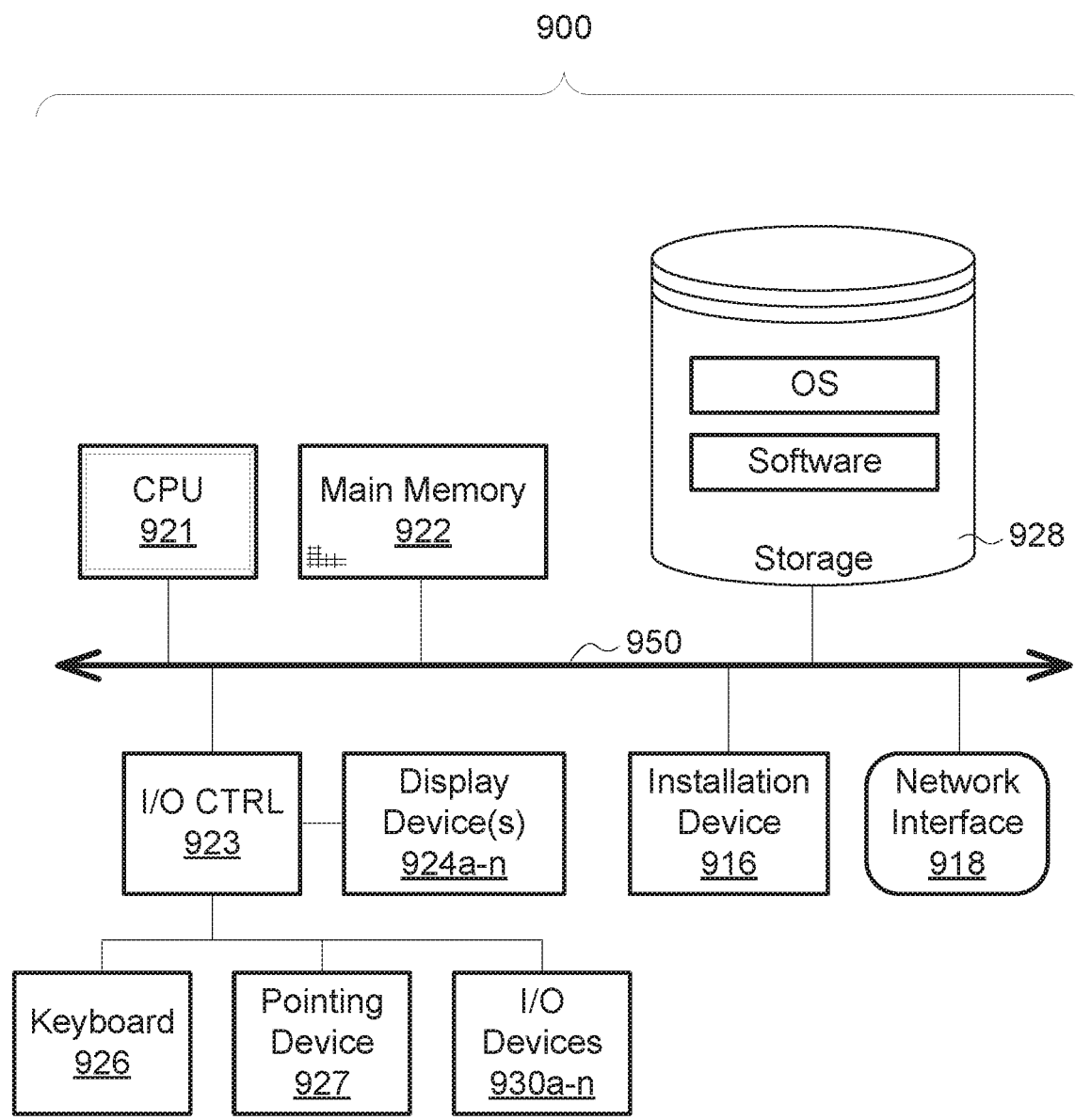
FIGS. 9C and 9D are block diagrams depicting embodiments of computing devices useful in connection with the methods and systems described herein.
Figure 9D:
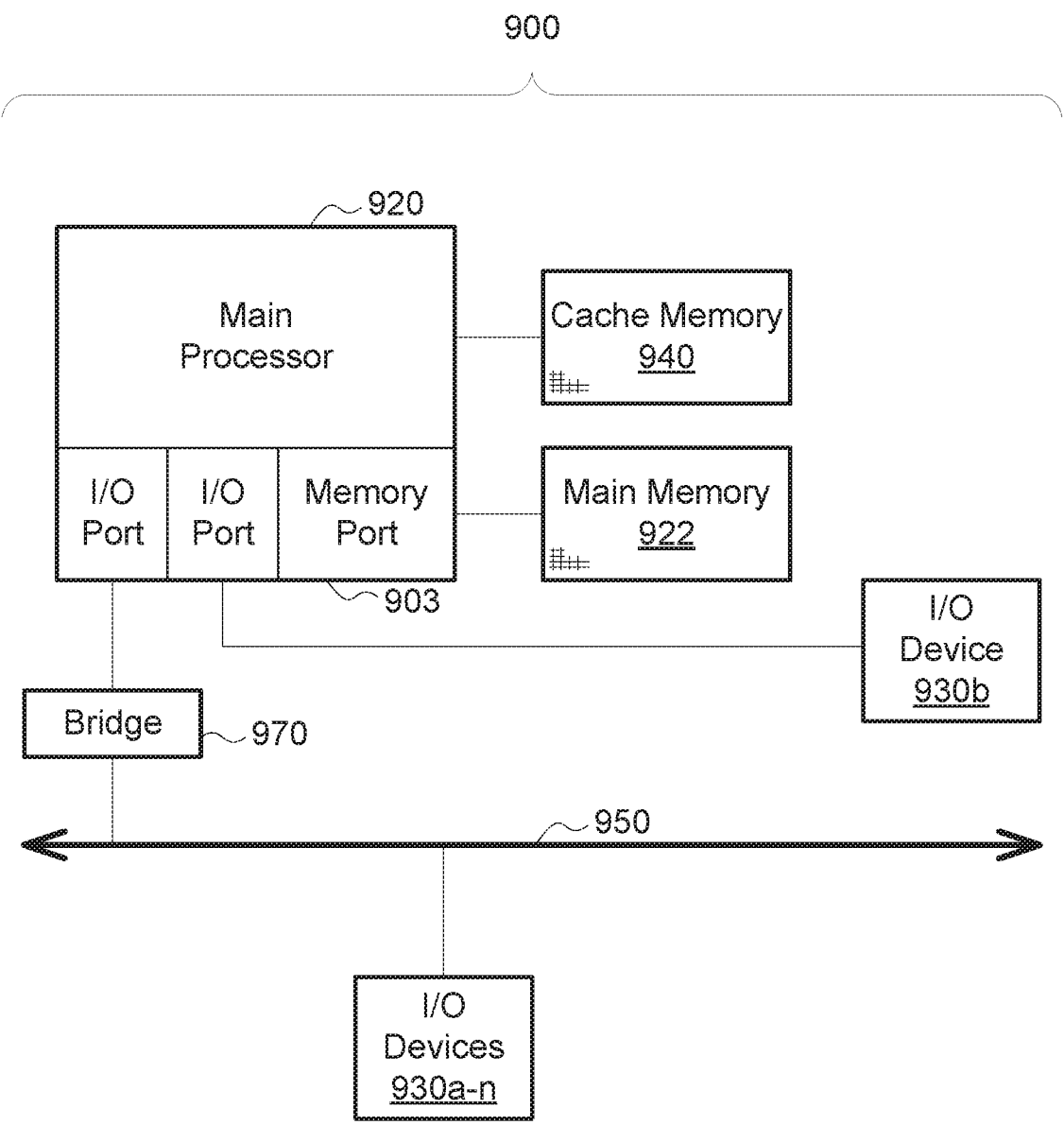

The client 902 and server 906 may be deployed as and/or executed on any type and form of computing device, e.g. a computer, network device or appliance capable of communicating on any type and form of network and performing the operations described herein. FIGS. 9C and 9D depict block diagrams of a computing device 900 useful for practicing an embodiment of the client 902 or a server 906. As shown in FIGS. 9C and 9D, each computing device 900 includes a central processing unit 921, and a main memory unit 922. As shown in FIG. 9C, a computing device 900 may include a storage device 928, an installation device 916, a network interface 918, an I/O controller 923, display devices 924a-924n, a keyboard 926 and a pointing device 927, e.g. a mouse. The storage device 928 may include, without limitation, an operating system, and/or software 920. As shown in FIG. 9D, each computing device 900 may also include additional optional elements, e.g. a memory port 903, a bridge 970, one or more input/output devices 930a-930n (generally referred to using reference numeral 930), and a cache memory 940 in communication with the central processing unit 921.

The central processing unit 921 is any logic circuitry that responds to and processes instructions fetched from the main memory unit 922. In many embodiments, the central processing unit 921 is provided by a microprocessor unit, e.g.: those manufactured by Intel Corporation of Mountain View, Calif.; those manufactured by Motorola Corporation of Schaumburg, Ill.; the ARM processor and TEGRA system on a chip (SoC) manufactured by Nvidia of Santa Clara, Calif.; the POWER7 processor, those manufactured by International Business Machines of White Plains, N.Y.; or those manufactured by Advanced Micro Devices of Sunnyvale, Calif. The computing device 900 may be based on any of these processors, or any other processor capable of operating as described herein. The central processing unit 921 may utilize instruction level parallelism, thread level parallelism, different levels of cache, and multi-core processors. A multi-core processor may include two or more processing units on a single computing component. Examples of multi-core processors include the AMD PHENOM IIX2, INTEL CORE i5 and INTEL CORE i7.

Main memory unit 922 may include one or more memory chips capable of storing data and allowing any storage location to be directly accessed by the microprocessor 921. Main memory unit 922 may be volatile and faster than storage 928 memory. Main memory units 922 may be Dynamic random access memory (DRAM) or any variants, including static random access memory (SRAM), Burst SRAM or SynchBurst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM). In some embodiments, the main memory 922 or the storage 928 may be non-volatile; e.g., non-volatile read access memory (NVRAM), flash memory non-volatile static RANI (nvSRAM), Ferroelectric RANI (FeRAM), Magnetoresistive RANI (MRAM), Phase-change memory (PRAM), conductive-bridging RAM (CBRAM), Silicon-Oxide-Nitride-Oxide-Silicon (SONOS), Resistive RAM (RRAM), Racetrack, Nano-RAM (NRAM), or Millipede memory. The main memory 922 may be based on any of the above described memory chips, or any other available memory chips capable of operating as described herein. In the embodiment shown in FIG. 9C, the processor 921 communicates with main memory 922 via a system bus 950 (described in more detail below). FIG. 9D depicts an embodiment of a computing device 900 in which the processor communicates directly with main memory 922 via a memory port 903. For example, in FIG. 9D the main memory 922 may be DRDRAM.

FIG. 9D depicts an embodiment in which the main processor 921 communicates directly with cache memory 940 via a secondary bus, sometimes referred to as a backside bus. In other embodiments, the main processor 921 communicates with cache memory 940 using the system bus 950. Cache memory 940 typically has a faster response time than main memory 922 and is typically provided by SRAM, BSRAM, or EDRAM. In the embodiment shown in FIG. 9D, the processor 921 communicates with various I/O devices 930 via a local system bus 950. Various buses may be used to connect the central processing unit 921 to any of the I/O devices 930, including a PCI bus, a PCI-X bus, or a PCI-Express bus, or a NuBus. For embodiments in which the I/O device is a video display 924, the processor 921 may use an Advanced Graphics Port (AGP) to communicate with the display 924 or the I/O controller 923 for the display 924. FIG. 9D depicts an embodiment of a computer 900 in which the main processor 921 communicates directly with I/O device 930b or other processors 921' via HYPERTRANSPORT, RAPIDIO, or INFINIBAND communications technology. FIG. 9D also depicts an embodiment in which local busses and direct communication are mixed: the processor 921 communicates with I/O device 930a using a local interconnect bus while communicating with I/O device 930b directly.

A wide variety of I/O devices 930a-930n may be present in the computing device 900. Input devices may include keyboards, mice, trackpads, trackballs, touchpads, touch mice, multi-touch touchpads and touch mice, microphones, multi-array microphones, drawing tablets, cameras, single-lens reflex camera (SLR), digital SLR (DSLR), CMOS sensors, accelerometers, infrared optical sensors, pressure sensors, magnetometer sensors, angular rate sensors, depth sensors, proximity sensors, ambient light sensors, gyroscopic sensors, or other sensors. Output devices may include video displays, graphical displays, speakers, headphones, inkjet printers, laser printers, and 3D printers.

Devices 930a-930n may include a combination of multiple input or output devices, including, e.g., Microsoft KINECT, Nintendo Wiimote for the WII, Nintendo WII U GAMEPAD, or Apple IPHONE. Some devices 930a-930n allow gesture recognition inputs through combining some of the inputs and outputs. Some devices 930a-930n provides for facial recognition which may be utilized as an input for different purposes including authentication and other commands. Some devices 930a-930n provides for voice recognition and inputs, including, e.g., Microsoft KINECT, SIRI for IPHONE by Apple, Google Now or Google Voice Search.

Additional devices 930a-930n have both input and output capabilities, including, e.g., haptic feedback devices, touchscreen displays, or multi-touch displays. Touchscreen, multi-touch displays, touchpads, touch mice, or other touch sensing devices may use different technologies to sense touch, including, e.g., capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices may allow two or more contact points with the surface, allowing advanced functionality including, e.g., pinch, spread, rotate, scroll, or other gestures. Some touchscreen devices, including, e.g., Microsoft PIXELSENSE or Multi-Touch Collaboration Wall, may have larger surfaces, such as on a table-top or on a wall, and may also interact with other electronic devices. Some I/O devices 930a-930n, display devices 924a-924n or group of devices may be augment reality devices. The I/O devices may be controlled by an I/O controller 923 as shown in FIG. 9C. The I/O controller may control one or more I/O devices, such as, e.g., a keyboard 926 and a pointing device 927, e.g., a mouse or optical pen. Furthermore, an I/O device may also provide storage and/or an installation medium 916 for the computing device 900. In still other embodiments, the computing device 900 may provide USB connections (not shown) to receive handheld USB storage devices. In further embodiments, an I/O device 930 may be a bridge between the system bus 950 and an external communication bus, e.g. a USB bus, a SCSI bus, a FireWire bus, an Ethernet bus, a Gigabit Ethernet bus, a Fibre Channel bus, or a Thunderbolt bus.

In some embodiments, display devices 924a-924n may be connected to I/O controller 923. Display devices may include, e.g., liquid crystal displays (LCD), thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays. Examples of 3D displays may use, e.g. stereoscopy, polarization filters, active shutters, or autostereoscopy. Display devices 924a-924n may also be a head-mounted display (HMD). In some embodiments, display devices 924a-924n or the corresponding I/O controllers 923 may be controlled through or have hardware support for OPENGL or DIRECTX API or other graphics libraries.

In some embodiments, the computing device 900 may include or connect to multiple display devices 924a-924n, which each may be of the same or different type and/or form. As such, any of the I/O devices 930a-930n and/or the I/O controller 923 may include any type and/or form of suitable hardware, software, or combination of hardware and software to support, enable or provide for the connection and use of multiple display devices 924a-924n by the computing device 900. For example, the computing device 900 may include any type and/or form of video adapter, video card, driver, and/or library to interface, communicate, connect or otherwise use the display devices 924a-924n. In one embodiment, a video adapter may include multiple connectors to interface to multiple display devices 924a-924n. In other embodiments, the computing device 900 may include multiple video adapters, with each video adapter connected to one or more of the display devices 924a-924n. In some embodiments, any portion of the operating system of the computing device 900 may be configured for using multiple displays 924a-924n. In other embodiments, one or more of the display devices 924a-924n may be provided by one or more other computing devices 900a or 900b connected to the computing device 900, via the network 904. In some embodiments software may be designed and constructed to use another computer's display device as a second display device 924a for the computing device 900. For example, in one embodiment, an Apple iPad may connect to a computing device 900 and use the display of the device 900 as an additional display screen that may be used as an extended desktop. One ordinarily skilled in the art will recognize and appreciate the various ways and embodiments that a computing device 900 may be configured to have multiple display devices 924a-924n.

Referring again to FIG. 9C, the computing device 900 may comprise a storage device 928 (e.g. one or more hard disk drives or redundant arrays of independent disks) for storing an operating system or other related software, and for storing application software programs such as any program related to the software 920. Examples of storage device 928 include, e.g., hard disk drive (HDD); optical drive including CD drive, DVD drive, or BLU-RAY drive; solid-state drive (SSD); USB flash drive; or any other device suitable for storing data. Some storage devices may include multiple volatile and non-volatile memories, including, e.g., solid state hybrid drives that combine hard disks with solid state cache. Some storage device 928 may be non-volatile, mutable, or read-only. Some storage device 928 may be internal and connect to the computing device 900 via a bus 950. Some storage device 928 may be external and connect to the computing device 900 via an I/O device 930 that provides an external bus. Some storage device 928 may connect to the computing device 900 via the network interface 918 over a network 904, including, e.g., the Remote Disk for MACBOOK AIR by Apple. Some client devices 900 may not require a non-volatile storage device 928 and may be thin clients or zero clients 902. Some storage device 928 may also be used as an installation device 916, and may be suitable for installing software and programs. Additionally, the operating system and the software can be run from a bootable medium, for example, a bootable CD, e.g. KNOPPIX, a bootable CD for GNU/Linux that is available as a GNU/Linux distribution from knoppix.net.

Client device 900 may also install software or application from an application distribution platform. Examples of application distribution platforms include the App Store for iOS provided by Apple, Inc., the Mac App Store provided by Apple, Inc., GOOGLE PLAY for Android OS provided by Google Inc., Chrome Webstore for CHROME OS provided by Google Inc., and Amazon Appstore for Android OS and KINDLE FIRE provided by Amazon.com, Inc. An application distribution platform may facilitate installation of software on a client device 902. An application distribution platform may include a repository of applications on a server 906 or a cloud 908, which the clients 902a-902n may access over a network 904. An application distribution platform may include application developed and provided by various developers. A user of a client device 902 may select, purchase and/or download an application via the application distribution platform.

Furthermore, the computing device 900 may include a network interface 918 to interface to the network 904 through a variety of connections including, but not limited to, standard telephone lines LAN or WAN links (e.g., 802.11, T1, T3, Gigabit Ethernet, Infiniband), broadband connections (e.g., ISDN, Frame Relay, ATM, Gigabit Ethernet, Ethernet-over-SONET, ADSL, VDSL, BPON, GPON, fiber optical including FiOS), wireless connections, or some combination of any or all of the above. Connections can be established using a variety of communication protocols (e.g., TCP/IP, Ethernet, ARCNET, SONET, SDH, Fiber Distributed Data Interface (FDDI), IEEE 802.11a/b/g/n/ac CDMA, GSM, WiMax and direct asynchronous connections). In one embodiment, the computing device 900 communicates with other computing devices 900' via any type and/or form of gateway or tunneling protocol e.g. Secure Socket Layer (SSL) or Transport Layer Security (TLS), or the Citrix Gateway Protocol manufactured by Citrix Systems, Inc. of Ft. Lauderdale, Fla. The network interface 918 may comprise a built-in network adapter, network interface card, PCMCIA network card, EXPRESSCARD network card, card bus network adapter, wireless network adapter, USB network adapter, modem or any other device suitable for interfacing the computing device 900 to any type of network capable of communication and performing the operations described herein.

A computing device 900 of the sort depicted in FIGS. 9B and 9C may operate under the control of an operating system, which controls scheduling of tasks and access to system resources. The computing device 900 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 2000, WINDOWS Server 2012, WINDOWS CE, WINDOWS Phone, WINDOWS XP, WINDOWS VISTA, and WINDOWS 7, WINDOWS RT, and WINDOWS 8 all of which are manufactured by Microsoft Corporation of Redmond, Wash.; MAC OS and iOS, manufactured by Apple, Inc. of Cupertino, Calif.; and Linux, a freely-available operating system, e.g. Linux Mint distribution ("distro") or Ubuntu, distributed by Canonical Ltd. of London, United Kingdom; or Unix or other Unix-like derivative operating systems; and Android, designed by Google, of Mountain View, Calif., among others. Some operating systems, including, e.g., the CHROME OS by Google, may be used on zero clients or thin clients, including, e.g., CHROMEBOOKS.

The computer system 900 can be any workstation, telephone, desktop computer, laptop or notebook computer, netbook, ULTRABOOK, tablet, server, handheld computer, mobile telephone, smartphone or other portable telecommunications device, media playing device, a gaming system, mobile computing device, or any other type and/or form of computing, telecommunications or media device that is capable of communication. The computer system 900 has sufficient processor power and memory capacity to perform the operations described herein. In some embodiments, the computing device 900 may have different processors, operating systems, and input devices consistent with the device. The Samsung GALAXY smartphones, e.g., operate under the control of Android operating system developed by Google, Inc. GALAXY smartphones receive input via a touch interface.

In some embodiments, the computing device 900 is a gaming system. For example, the computer system 900 may comprise a PLAYSTATION 3, or PERSONAL PLAYSTATION PORTABLE (PSP), or a PLAYSTATION VITA device manufactured by the Sony Corporation of Tokyo, Japan, a NINTENDO DS, NINTENDO 3DS, NINTENDO WII, or a NINTENDO WII U device manufactured by Nintendo Co., Ltd., of Kyoto, Japan, an XBOX 360 device manufactured by the Microsoft Corporation of Redmond, Wash.

In some embodiments, the computing device 900 is a digital audio player such as the Apple IPOD, IPOD Touch, and IPOD NANO lines of devices, manufactured by Apple Computer of Cupertino, Calif. Some digital audio players may have other functionality, including, e.g., a gaming system or any functionality made available by an application from a digital application distribution platform. For example, the IPOD Touch may access the Apple App Store. In some embodiments, the computing device 900 is a portable media player or digital audio player supporting file formats including, but not limited to, MP3, WAV, M4A/AAC, WMA Protected AAC, AIFF, Audible audiobook, Apple Lossless audio file formats and .mov, .m4v, and .mp4 MPEG-4 (H.264/MPEG-4 AVC) video file formats.

In some embodiments, the computing device 900 is a tablet e.g. the IPAD line of devices by Apple; GALAXY TAB family of devices by Samsung; or KINDLE FIRE, by Amazon.com, Inc. of Seattle, Wash. In other embodiments, the computing device 900 is an eBook reader, e.g. the KINDLE family of devices by Amazon.com, or NOOK family of devices by Barnes & Noble, Inc. of New York City, N.Y.

In some embodiments, the communications device 902 includes a combination of devices, e.g. a smartphone combined with a digital audio player or portable media player. For example, one of these embodiments is a smartphone, e.g. the IPHONE family of smartphones manufactured by Apple, Inc.; a Samsung GALAXY family of smartphones manufactured by Samsung, Inc.; or a Motorola DROID family of smartphones. In yet another embodiment, the communications device 902 is a laptop or desktop computer equipped with a web browser and a microphone and speaker system, e.g. a telephony headset. In these embodiments, the communications devices 902 are web-enabled and can receive and initiate phone calls. In some embodiments, a laptop or desktop computer is also equipped with a webcam or other video capture device that enables video chat and video call. In some embodiments, the communication device 902 is a wearable mobile computing device including but not limited to Google Glass and Samsung Gear.

In some embodiments, the status of one or more machines 902, 906 in the network 904 is monitored, generally as part of network management. In one of these embodiments, the status of a machine may include an identification of load information (e.g., the number of processes on the machine, CPU and memory utilization), of port information (e.g., the number of available communication ports and the port addresses), or of session status (e.g., the duration and type of processes, and whether a process is active or idle). In another of these embodiments, this information may be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the systems and methods disclosed herein.

The description herein including modules emphasizes the structural independence of the aspects of the controller, and illustrates one grouping of operations and responsibilities of the controller. Other groupings that execute similar overall operations are understood within the scope of the present application. Modules may be implemented in hardware and/or as computer instructions on a non-transient computer readable storage medium, and modules may be distributed across various hardware or computer based components.

Example and non-limiting module implementation elements include sensors providing any value determined herein, sensors providing any value that is a precursor to a value determined herein, datalink and/or network hardware including communication chips, oscillating crystals, communication links, cables, twisted pair wiring, coaxial wiring, shielded wiring, transmitters, receivers, and/or transceivers, logic circuits, hard-wired logic circuits, reconfigurable logic circuits in a particular non-transient state configured according to the module specification, any actuator including at least an electrical, hydraulic, or pneumatic actuator, a solenoid, an op-amp, analog control elements (springs, filters, integrators, adders, dividers, gain elements), and/or digital control elements.

Non-limiting examples of various embodiments are disclosed herein. Features from one embodiments disclosed herein may be combined with features of another embodiment disclosed herein as someone of ordinary skill in the art would understand.

As utilized herein, the terms "approximately," "about," "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described without restricting the scope of these features to the precise numerical ranges provided. Accordingly, these terms should be interpreted as indicating that insubstantial or inconsequential modifications or alterations of the subject matter described and are considered to be within the scope of the disclosure.

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It should be noted that the orientation of various elements may differ according to other exemplary embodiments, and that such variations are intended to be encompassed by the present disclosure. It is recognized that features of the disclosed embodiments can be incorporated into other disclosed embodiments.

It is important to note that the constructions and arrangements of apparatuses or the components thereof as shown in the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present disclosure.

While various inventive embodiments have been described and illustrated herein, those of ordinary skill in the art will readily envision a variety of other mechanisms and/or structures for performing the function and/or obtaining the results and/or one or more of the advantages described herein, and each of such variations and/or modifications is deemed to be within the scope of the inventive embodiments described herein. More generally, those skilled in the art will readily appreciate that, unless otherwise noted, any parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, the technology described herein may be embodied as a method, of which at least one example has been provided. The acts performed as part of the method may be ordered in any suitable way unless otherwise specifically noted. Accordingly, embodiments may be constructed in which acts are performed in an order different than illustrated, which may include performing some acts simultaneously, even though shown as sequential acts in illustrative embodiments.

The indefinite articles "a" and "an," as used herein in the specification and in the claims, unless clearly indicated to the contrary, should be understood to mean "at least one." As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

What is claimed is:

1. A system for processing immobilization molds for application of treatment, comprising:
   a mold model generator executable on a computing system having one or more processor and memory, configured to generate a three-dimensional mold model of an immobilization mold within with a subject is to be positioned for application of a treatment, the three-dimensional dimensional mold model generated by:
   subtracting, from a first composite space of the three-dimensional mold model, a second composite space corresponding to a three-dimensional scan of at least a portion of the subject to define an opening within the three-dimensional mold model;
   removing, from the three-dimensional mold model, to define an imprint in the opening, a first portion along a first axis in which the subject is to enter the immobilization mold;
   identifying, from a second portion of the three-dimensional mold model remaining after the removal of the first portion, one or more inward protrusions into the imprint of the three-dimensional mold model relative to a second axis intersecting the first axis; and removing, from the three-dimensional mold model, the identified one or more inward protrusions relative to the second axis.

2. The system of claim 1, further comprising an accessory positioner executable on the computing system, configured to:

identify, within the three-dimensional mold model, a position at which to insert an accessory into the immobilization mold, the accessory including at least one of a tensioner, an anchoring mechanism, a sensor, a probe, or a treatment application device;

determine a third portion about the position within the three-dimensional mold model corresponding to dimensions of the accessory to be inserted; and remove the third portion from at least a part of the second portion of the three-dimensional mold model for insertion of the accessory.

3. The system of claim 1, further comprising an accessory positioner executable on the computing system, configured to identify, within the three-dimensional mold model, a position at which to insert an accessory into the immobilization mold, the accessory including at least one of a tensioner, an anchoring mechanism, a sensor, a probe, or a treatment application device;

determine a third portion about the position within the three-dimensional mold model corresponding to dimensions of the accessory to be inserted; and add the third portion to the three-dimensional mold model for insertion of the accessory.

4. The system of claim 1, wherein the mold model generator is further configured to generate the three-dimensional mold model by:

identifying a plurality of two-dimensional slices of the three-dimensional mold model after subtracting the second composite space; and for each two-dimensional slice of the three-dimensional mold model after subtracting the second composite space:

identifying a first section and a second section to divide the opening about the first axis;

determining a first global extremum from the first section and a second global extremum from the second section within the opening relative to the second axis; and removing, from the three-dimensional mold, the first portion in the first section from the first global extremum relative to the first axis and the first portion in the second section from the second global extremum relative to the first axis.

5. The system of claim 1, wherein the mold model generator is further configured to generate the three-dimensional mold model by:

identifying a plurality of two-dimensional slices of the three-dimensional mold model after subtracting the second composite space; and for each two-dimensional slice of the three-dimensional mold model after subtracting the second composite space:

identifying a first section and a second section to divide the opening about the first axis;

determining a first plurality of extrema in the first section within the opening and a second plurality of extrema in the second section within the opening relative to the second axis;

identifying, in the first section, a first inward protrusion of the one or more inward protrusions in the three-dimensional mold model at the two-dimensional slice based on the first plurality of extrema;

identifying, in the second section, a second inward protrusion of the one or more inward protrusions in the three-dimensional mold model at the two-dimensional slice based on the second plurality of extrema; and remove the first inward protrusion and the second inward protrusion from the two-dimensional slice of the three-dimensional mold model.

6. The system of claim 1, wherein the mold model generator is further configured to generate the three-dimensional mold model by:

identifying a plurality of two-dimensional slices of the three-dimensional mold model after subtracting the second composite space;

identifying, for each two-dimensional slice of the three-dimensional mold model after subtracting the second composite space, one or more contiguous portions of the opening defined by subtracting the second composite space corresponding to the three-dimensional scan of the subject; and identifying, for each contiguous portion, a first section and a second section to divide the contiguous portion to remove the first portion and one or more inward protrusions.

7. The system of claim 1, further comprising a mold model optimizer executable on the computing system configured to:

identify a manufacturing modality of a mold generator to manufacture the immobilization mold in accordance with the three-dimensional model, the manufacturing modality including at least one of a subtractive manufacturing or an additive manufacturing; and modify the three-dimensional mold model based on the identified manufacturing modality of the mold generator.

8. The system of claim 1, further comprising a mold model optimizer executable on the computing system configured to apply an image processing technique to the three-dimensional mold model after subtracting the second composite space and removing the first portion and the one or more inward protrusions, the image processing technique including at least one of an autofix function, a smoothing filter, a mesh reduction function, or a depth contrast adjustment.

9. The system of claim 1, wherein the mold model generator is further configured to provide the three-dimensional mold model to a mold generator device to manufacture the immobilization mold in accordance with the three-dimensional mold model.

10. The system of claim 1, further comprising:

an imager interface executable on the computing system configured to acquire, from an imaging device, the three-dimensional scan of the subject; and an image converter executable on the computing system configured to convert the three-dimensional scan of the subject to the second composite space to subtract from the first composite space of the three-dimensional mold model.

11. A method of processing immobilization molds for application of treatment, comprising:

generating, by a computing system having one or more processors, a three-dimensional mold model of immobilization mold within with a subject is to be positioned for application of a treatment, the three-dimensional dimensional mold model generated by:
  subtracting, from a first composite space of the three-dimensional mold model, a second composite space corresponding to a three-dimensional scan of at least a portion of the subject to define an opening within the three-dimensional mold model;
  removing, from the three-dimensional mold model, to define an imprint in the opening, a first portion along a first axis in which the subject is to enter the immobilization mold;
  identifying, from a second portion of the three-dimensional mold model remaining after the removal of the first portion, one or more inward protrusions into the imprint of the three-dimensional mold model relative to a second axis intersecting the first axis; and
  removing, from the three-dimensional mold model, the identified one or more inward protrusions relative to the second axis.

12. The method of claim 11, further comprising:
  identifying, by the computing system, within the three-dimensional mold model, a position at which to insert an accessory into the immobilization mold, the accessory including at least one of a tensioner, an anchoring mechanism, a sensor, a probe, or a treatment application device;
  determining, by the computing system, a third portion about the position within the three-dimensional mold model corresponding to dimensions of the accessory to be inserted; and
  removing, by the computing system, the third portion of at least a part of the second portion of the three-dimensional mold model for insertion of the accessory.

13. The method of claim 11, further comprising:
  identifying, by the computing system, within the three-dimensional mold model, a position at which to insert an accessory into the immobilization mold, the accessory including at least one of a tensioner, an anchoring mechanism, a sensor, a probe, or a treatment application device;
  determining, by the computing system, a third portion about the position within the three-dimensional mold model corresponding to dimensions of the accessory to be inserted; and
  adding, by the computing system, the third portion to the three-dimensional mold model for insertion of the accessory.

14. The method of claim 11, wherein generating the three-dimensional mold further comprises:
  identifying, by the computing system, a plurality of two-dimensional slices of the three-dimensional mold model after subtracting the second composite space; and
  for each two-dimensional slice of the three-dimensional mold model after subtracting the second composite space:
    identifying, by the computing system, a first section and a second section of to divide the opening about the first axis;
    determining, by the computing system, a first global extremum from the first section and a second global extremum from the second section within the opening relative to the second axis; and
    removing, by the computing system, from the three-dimensional mold, the first portion in the first section from the first global extremum relative to the first axis and the first portion in the second section from the second global extremum relative to the first axis.

15. The method of claim 11, wherein generating the three-dimensional mold further comprises:
  identifying, by the computing system, a plurality of two-dimensional slices of the three-dimensional mold model after subtracting the second composite space; and
  for each two-dimensional slice of the three-dimensional mold model after subtracting the second composite space:
    identifying, by the computing system, a first section and a second section to divide the opening about the first axis;
    determining, by the computing system, a first plurality of extrema in the first section within the opening and a second plurality of extrema in the second section within the opening relative to the second axis;
    identifying, by the computing system, in the first section, a first inward protrusion of the one or more inward protrusions in the three-dimensional mold model at the two-dimensional slice based on the first plurality of extrema;
    identifying, by the computing system, in the second section, a second inward protrusion of the one or more inward protrusions in the three-dimensional mold model at the two-dimensional slice based on the second plurality of extrema; and
    removing, by the computing system, the first inward protrusion and the second inward protrusion from the two-dimensional slice of the three-dimensional mold model.

16. The method of claim 11, wherein generating the three-dimensional mold further comprises:
  identifying, by the computing system, a plurality of two-dimensional slices of the three-dimensional mold model after subtracting the second composite space;
  identifying, by the computing system, for each two-dimensional slice of the three-dimensional mold model after subtracting the second composite space, one or more contiguous portions of the opening defined by subtracting the second composite space corresponding to the three-dimensional scan of the subject; and
  identifying, by the computing system, for each contiguous portion, a first section and a second section to divide the contiguous portion to remove the first portion and one or more inward protrusions.

17. The method of claim 11, further comprising identifying, by the computing system, a manufacturing modality of a mold generator to manufacture the immobilization mold in accordance with the three-dimensional model, the manufacturing modality including at least one of a subtractive manufacturing or an additive manufacturing; and
  modifying, by the computing system, the three-dimensional mold model based on the identified manufacturing modality of the mold generator.

18. The method of claim 11, further comprising applying, by the computing system, an image processing technique to the three-dimensional mold model after subtracting the second composite space and the removal the first portion and the one or more inward protrusions, the image processing technique including at least one of an autofix function, a smoothing filter, a mesh reduction function, or a depth contrast adjustment.

19. The method of claim 11, further comprising
providing, by the computing system, the three-dimensional mold model to a mold generator device to manufacture the immobilization mold in accordance with the three-dimensional mold model.

20. The method of claim 11, further comprising
acquiring, by the computing system, from an imaging device, the three-dimensional scan of the subject; and
converting, by the computing system, the three-dimensional scan of the subject to the second composite space to subtract from the first composite space of the three-dimensional mold model.

\* \* \* \* \*